US008148340B2

(12) United States Patent
Krieg et al.

(10) Patent No.: US 8,148,340 B2
(45) Date of Patent: Apr. 3, 2012

(54) IMMUNOMODULATORY OLIGONUCLEOTIDES

(75) Inventors: Arthur M. Krieg, Wellesley, MA (US); Dennis Klinman, Potomac, MD (US); Alfred D. Steinberg, Potomac, MD (US)

(73) Assignees: The United States of America as represented by the Department of Health and Human Services, Washington, DC (US); University of Iowa Research Foundation, Iowa City, IA (US); Pfizer Inc., New York, NY (US)

( * ) Notice: Subject to any disclaimer, the term of this patent is extended or adjusted under 35 U.S.C. 154(b) by 610 days.

(21) Appl. No.: 10/888,089

(22) Filed: Jul. 9, 2004

(65) Prior Publication Data
US 2005/0037403 A1  Feb. 17, 2005

Related U.S. Application Data

(60) Continuation of application No. 10/690,495, filed on Oct. 21, 2003, now abandoned, which is a continuation of application No. 09/415,142, filed on Oct. 9, 1999, now abandoned, which is a division of application No. 08/386,063, filed on Feb. 7, 1995, now Pat. No. 6,194,388, which is a continuation-in-part of application No. 08/276,358, filed on Jul. 15, 1994, now abandoned.

(51) Int. Cl.
C12N 15/11 (2006.01)
C07H 21/02 (2006.01)
(52) U.S. Cl. .................................... 514/44 R; 536/23.1
(58) Field of Classification Search ................. 536/23.1; 514/44 R
See application file for complete search history.

(56) References Cited

U.S. PATENT DOCUMENTS

| | | | |
|---|---|---|---|
| 4,452,775 A | 6/1984 | Kent | |
| 4,981,684 A | 1/1991 | MacKenzie et al. | |
| 5,075,109 A * | 12/1991 | Tice et al. .................. | 424/193.1 |
| 5,178,860 A | 1/1993 | MacKenzie et al. | |
| 5,543,152 A | 8/1996 | Webb et al. | |
| 5,595,756 A | 1/1997 | Bally et al. | |
| 5,663,153 A | 9/1997 | Hutcherson et al. | |
| 5,679,354 A | 10/1997 | Morein et al. | |
| 5,705,109 A * | 1/1998 | Parks .......................... | 264/80 |
| 5,705,385 A | 1/1998 | Bally et al. | |
| 5,723,335 A * | 3/1998 | Hutcherson et al. .......... | 435/375 |
| 5,753,613 A | 5/1998 | Ansell et al. | |
| 5,785,992 A | 7/1998 | Ansell et al. | |
| 5,814,335 A | 9/1998 | Webb et al. | |
| 5,858,784 A | 1/1999 | Debs et al. | |
| 5,929,226 A | 7/1999 | Padmapriya et al. | |
| 5,965,542 A | 10/1999 | Wasan et al. | |
| 5,968,909 A | 10/1999 | Agrawal et al. | |
| 5,976,567 A | 11/1999 | Wheeler et al. | |
| 5,981,501 A | 11/1999 | Wheeler et al. | |
| 6,004,534 A | 12/1999 | Langer et al. | |
| 6,027,726 A | 2/2000 | Ansell | |
| 6,027,732 A | 2/2000 | Morein et al. | |
| 6,030,954 A | 2/2000 | Wu et al. | |
| 6,110,745 A | 8/2000 | Zhang et al. | |
| 6,121,434 A | 9/2000 | Peyman et al. | |
| 6,191,257 B1 | 2/2001 | Ledley et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,221,882 B1 | 4/2001 | Macfarlane | |
| 6,239,116 B1 | 5/2001 | Krieg et al. | |
| 6,248,720 B1 | 6/2001 | Mathiowitz et al. | |
| 6,339,068 B1 | 1/2002 | Krieg et al. | |
| 6,348,312 B1 | 2/2002 | Peyman et al. | |
| 6,399,630 B1 | 6/2002 | Macfarlane | |
| 6,406,705 B1 | 6/2002 | Davis et al. | |
| 6,429,199 B1 | 8/2002 | Krieg et al. | |
| 6,479,504 B1 | 11/2002 | Macfarlane et al. | |
| 6,498,148 B1 | 12/2002 | Raz | |
| 6,514,948 B1 | 2/2003 | Raz et al. | |
| 6,521,637 B2 | 2/2003 | Macfarlane | |
| 6,534,062 B2 | 3/2003 | Raz et al. | |
| 6,544,518 B1 | 4/2003 | Friede et al. | |
| 6,552,006 B2 | 4/2003 | Raz et al. | |

(Continued)

FOREIGN PATENT DOCUMENTS
EP  0 302 758 A1  2/1989
(Continued)

OTHER PUBLICATIONS

Branda et al 1996 Journal of Laboratory and Clinical Medicine pp. 335.*
Kuramato et al 1992 Jpn. J. Cancer Res. vol. 83, 1128-1131 see pp. 1128-1131.*
Yamamoto et al 1992 Microbiol. Immunol. vol. 36 No. 9 p. 992.*
Heeg et al 2000 International Archives of Allergy and Immunology pp. 87-97.*
Yamada et al 2002 Journal of Immunology pp. 5590-5594.*
Goldberg et al 2000 Immunology Letters.73:13-18.*
Li et al, Vaccine 2003, 21:3319-3329.*
Chu et al 1997 CpG Oligodeoxynucleotides Act as Adjuvants that Switch on T Helper 1 (TH1) Immunity pp. 1623-1630.*
Kataoka et al. 1992 Jpn J. Cancer Res vol. 83 pp. 244-247.*
Goodchild et al 1990 The American Chemical Society, vol. 1, No. 3 pp. 165-182.*

(Continued)

Primary Examiner — Gary Nickol
Assistant Examiner — Nina Archie
(74) Attorney, Agent, or Firm — Wolf, Greenfield & Sacks, P.C.; Gregg C. Benson

(57) ABSTRACT

Oligonucleotides containing unthylated CpG dinucleotides and therapeutic utilities based on their ability to stimulate an immune response in a subject are disclosed. Also disclosed are therapies for treating diseases associated with immune system activation that are initiated by unthylated CpG dinucleotides in a subject comprising administering to the subject oligonucleotides that do not contain unmethylated CpG sequences (i.e. methylated CpG sequences or no CpG sequence) to outcompete unmethylated CpG nucleic acids for binding. Further disclosed are methylated CpG containing dinucleotides for use antisense therapies or as in vivo hybridization probes, and immunoinhibitory oligonucleotides for use as antiviral therapeutics.

7 Claims, No Drawings

U.S. PATENT DOCUMENTS

| | | |
|---|---|---|
| 6,558,670 B1 | 5/2003 | Friede et al. |
| 6,562,798 B1 | 5/2003 | Schwartz |
| 6,589,940 B1 | 7/2003 | Raz et al. |
| 6,605,708 B1 | 8/2003 | Habus et al. |
| 6,610,661 B1 | 8/2003 | Carson et al. |
| 6,613,751 B2 | 9/2003 | Raz et al. |
| 6,620,805 B1 | 9/2003 | Takle et al. |
| 6,630,455 B1 | 10/2003 | Mitchell |
| 6,653,292 B1 | 11/2003 | Krieg et al. |
| 6,727,230 B1 | 4/2004 | Hutcherson et al. |
| 6,821,957 B2 | 11/2004 | Krieg et al. |
| 6,835,395 B1 | 12/2004 | Semple et al. |
| 6,943,240 B2 | 9/2005 | Bauer et al. |
| 6,949,520 B1 | 9/2005 | Hartmann et al. |
| 6,951,845 B2 | 10/2005 | Carson et al. |
| 7,001,890 B1 | 2/2006 | Wagner et al. |
| 7,129,222 B2 | 10/2006 | Van Nest et al. |
| 2002/0055477 A1 | 5/2002 | Nest et al. |
| 2002/0091097 A1 | 7/2002 | Bratzler et al. |
| 2002/0164341 A1 | 11/2002 | Davis et al. |
| 2003/0022852 A1 | 1/2003 | Nest et al. |
| 2003/0026801 A1 | 2/2003 | Weiner et al. |
| 2003/0027782 A1 | 2/2003 | Carson et al. |
| 2003/0050261 A1 | 3/2003 | Krieg et al. |
| 2003/0050268 A1 | 3/2003 | Krieg et al. |
| 2003/0059773 A1 | 3/2003 | Van Nest et al. |
| 2003/0078223 A1 | 4/2003 | Raz et al. |
| 2003/0091599 A1 | 5/2003 | Davis et al. |
| 2003/0092663 A1 | 5/2003 | Raz |
| 2003/0100527 A1 | 5/2003 | Krieg et al. |
| 2003/0109469 A1 | 6/2003 | Carson et al. |
| 2003/0119773 A1 | 6/2003 | Raz et al. |
| 2003/0119774 A1 | 6/2003 | Foldvari et al. |
| 2003/0129251 A1 | 7/2003 | Van Nest et al. |
| 2003/0133988 A1 | 7/2003 | Fearon et al. |
| 2003/0139364 A1 | 7/2003 | Krieg et al. |
| 2003/0148316 A1 | 8/2003 | Lipford et al. |
| 2003/0148976 A1 | 8/2003 | Krieg et al. |
| 2003/0181406 A1 | 9/2003 | Schetter et al. |
| 2003/0186921 A1 | 10/2003 | Carson et al. |
| 2003/0191079 A1 | 10/2003 | Krieg et al. |
| 2003/0203861 A1 | 10/2003 | Carson et al. |
| 2003/0212026 A1 | 11/2003 | Krieg et al. |
| 2003/0224010 A1 | 12/2003 | Davis et al. |
| 2003/0232074 A1 | 12/2003 | Lipford et al. |
| 2003/0232780 A1 | 12/2003 | Carson et al. |
| 2003/0232856 A1 | 12/2003 | Macfarlane |
| 2004/0006010 A1 | 1/2004 | Carson et al. |
| 2004/0006034 A1 | 1/2004 | Raz et al. |
| 2004/0009949 A1 | 1/2004 | Krieg |
| 2004/0030118 A1 | 2/2004 | Wagner et al. |
| 2004/0053880 A1 | 3/2004 | Krieg |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092472 A1 | 5/2004 | Krieg |
| 2004/0106568 A1 | 6/2004 | Krieg et al. |
| 2004/0131628 A1 | 7/2004 | Bratzler et al. |
| 2004/0132685 A1 | 7/2004 | Krieg et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0157791 A1 | 8/2004 | Dow et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0247662 A1 | 12/2004 | Dow et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0013812 A1 | 1/2005 | Dow et al. |
| 2005/0032734 A1 | 2/2005 | Davis et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0169888 A1 | 8/2005 | Hartmann et al. |
| 2005/0171047 A1 | 8/2005 | Krieg et al. |
| 2005/0176672 A1 | 8/2005 | Scheule et al. |
| 2005/0181035 A1 | 8/2005 | Dow et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0215500 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0249794 A1 | 11/2005 | Semple et al. |
| 2005/0250726 A1 | 11/2005 | Krieg et al. |
| 2005/0256073 A1 | 11/2005 | Lipford et al. |
| 2005/0267057 A1 | 12/2005 | Krieg |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0172966 A1 | 8/2006 | Lipford et al. |
| 2006/0188913 A1 | 8/2006 | Krieg et al. |
| 2006/0189550 A1 | 8/2006 | Jiang et al. |
| 2006/0211639 A1 | 9/2006 | Bratzler et al. |
| 2006/0211644 A1 | 9/2006 | Krieg et al. |
| 2006/0223769 A1 | 10/2006 | Dow et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |

| | | | |
|---|---|---|---|
| 2007/0129320 A9 | 6/2007 | Davis et al. | |
| 2007/0142315 A1 | 6/2007 | Forsbach et al. | |
| 2007/0184465 A1 | 8/2007 | Wagner et al. | |
| 2007/0202128 A1 | 8/2007 | Krieg et al. | |
| 2007/0224210 A1 | 9/2007 | Krieg et al. | |
| 2007/0232622 A1 | 10/2007 | Lipford et al. | |

FOREIGN PATENT DOCUMENTS

| | | | |
|---|---|---|---|
| EP | 0 468 520 A2 | | 1/1992 |
| WO | WO 90/14822 A1 | | 12/1990 |
| WO | WO/94/02595 | * | 2/1995 |
| WO | WO 95/24929 A2 | | 9/1995 |
| WO | WO 96/40162 A1 | | 12/1996 |
| WO | WO 97/03702 A1 | | 2/1997 |
| WO | WO 97/30731 A3 | | 8/1997 |
| WO | WO 97/42975 A2 | | 11/1997 |
| WO | WO 03/000232 A2 | | 1/2003 |

OTHER PUBLICATIONS

Tokunaga et al. 1992 Microbiol. Immunol., vol. 36, No. 1 pp. 55-66.*
Gura. Science vol. 270, p. 575-577, 1995.*
Kataoka et al. 1992 Jpn J. Cancer Res vol. 83 pp. 244-247.*
Goodchild et al 1990 The American Chemical Society, vol. 1, No. 3 pp. 165-182.*
Tokunaga et al. 1992 Microbiol. Immunol., vol. 36, No. 1 pp. 55-66.*
Katoaka et al 1992 Jpn Cancer Res. pp. 240-247.*
Yamamoto et al Journal of Immunology 1992 vol. 148 pp. 4072-4076.*
Yamamoto et al 1994 Antisense Research and Development. Summer, 4(2): 119-122.*
Iho et al The Journal of Immunology, 1999, 163: 3642-3652.*
Sommer et al Infection and Immunity vol. 72 No. 2 pp. 1029-1035.*
Agrawal et al., Absorption, tissue distribution and in vivo stability in rats of a hybrid antisense oligonucleotide following oral administration. Biochem Pharmacol. Aug. 8, 1995;50(4):571-6.
Agrawal et al., Pharmacokinetics, biodistribution, and stability of oligodeoxynucleotide phosphorothioates in mice. Proc Natl Acad Sci U S A. Sep. 1, 1991;88(17):7595-9.
Agrawal et al., Pharmacokinetics of antisense oligonucleotides. Clin Pharmacokinet. Jan. 1995;28(1):7-16.
Agrawal et al., Antisense oligonucleotides: towards clinical trials. Trends in Biotechnology, 1996; 14: 376-87.
Anitescu et al., Interleukin-10 functions in vitro and in vivo to inhibit bacterial DNA-induced secretion of interleukin-12. J Interferon Cytokine Res. Dec. 1997;17(12):781-8.
Ballas et al., Induction of NK activity in murine and human cells by CpG motifs in oligodeoxynucleotides and bacterial DNA. J Immunol. Sep. 1, 1996;157(5):1840-5.
Bowersock et al., Evaluation of an orally administered vaccine, using hydrogels containing bacterial exotoxins of Pasteurella haemolytica, in cattle. Am J Vet Res. Apr. 1994;55(4):502-9.
Chace et al., Bacterial DNA-induced NK cell IFN-gamma production is dependent on macrophage secretion of IL-12. Clin Immunol Immunopathol. Aug. 1997;84(2):185-93.
Chang et al., The effect of CpG-oligodeoxynucleotides with different backbone structures and 3' hexameric deoxyriboguanosine run conjugation on the treatment of asthma in mice. J Allergy Clin Immunol. 2004;113(2):S323. Abstract 1196.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Chu et al., CpG oligodeoxynucleotides act as adjuvants that switch on T helper 1 (Th1) immunity. J Exp Med. Nov. 17, 1997;186(10):1623-31.
Cohen, Selective anti-gene therapy for cancer: principles and prospects. Tohoku J Exp Med. Oct. 1992;168(2):351-9.
Cowdery et al., Bacterial DNA induces NK cells to produce IFN-gamma in vivo and increases the toxicity of lipopolysaccharides. J Immunol. Jun. 15, 1996;156(12):4570-5.
Crooke et al., Phosphorothioate Oligonucleotides. Therapeut Apps. 1995;ch5:63-84.

Cryz et al., European Commission COST/STD Initiative. Report of the expert panel VII. Vaccine delivery systems. Vaccine. May 1996;14(7):665-90.
Eldridge et al., Biodegradable microspheres as a vaccine delivery system. Mol Immunol. Mar. 1991;28(3):287-94. Abstract Only.
Fraley et al., New generation liposomes: the engineering of an efficient vehicle for intracellular delivery of nucleic acids. Trends. Biochem Sci. 1981;6:77-80.
Gallichan et al., Specific secretory immune responses in the female genital tract following intranasal immunization with a recombinant adenovirus expressing glycoprotein B of herpes simplex virus. Vaccine. Nov. 1995;13(16):1589-95.
Gao et al., Bacterial DNA and lipopolysaccharide induce synergistic production of TNF-alpha through a post-transcriptional mechanism. J Immunol. Jun. 1, 2001;166(11):6855-60.
Garegg et al., Nucleoside H-phosphonates. IV. Automated solid phase synthesis of oligoribonucleotides by the hydrogenphosphonate approach. Tetrahedron Lett. 1986; 27(34):4055-8.
Goodman et al., Selective modulation of elements of the immune system by low molecular weight nucleosides. J Pharmacol Exp Ther. Sep. 1995;274(3):1552-7.
Gregoriadis et al., Liposomes for drugs and vaccines. Trends Biotechnol. 1985;3:235-41.
Gregoriadis et al., Engineering liposomes for drug delivery: progress and problems. Trends Biotechnol. Dec. 1995;13(12):527-37.
Hadden et al., Immunostimulants. Trends Pharmacol Sci. May 1993;14(5):169-74.
Hahm et al., Efficacy of polyadenylic.polyuridylic acid in the treatment of chronic active hepatitis B. Int J Immunopharmacol. Mar. 1994;16(3):217-25.
Halpern et al., Bacterial DNA induces murine interferon-gamma production by stimulation of interleukin-12 and tumor necrosis factor-alpha. Cell Immunol. Jan. 10, 1996;167(1):72-8.
Hudson et al., Nucleic acid dendrimers: Novel biopolymer structures. J Am Chem Soc. 1993;115:2119-24.
Iversen et al., In vivo studies with phosphorothioate oligonucleotides: pharmacokinetics prologue. Anticancer Drug Des. Dec. 1991;6(6):531-8.
Jäschke et al., Automated incorporation of polyethylane glycol into synthetic oligonucleotides. Tetrahedron Lett. 1993;34(2):301-4.
Kataoka et al., Antitumor activity of synthetic oligonucleotides with sequences from cDNA encoding proteins of Mycobacterium bovis BCG. Jpn J Cancer Res. Mar. 1992;83(3):244-7.
Kataoka et al., Immunotherapeutic potential in guinea pig tumor model of deoxyribonucleic acid from Mycobacterium bovis BCG complexed with poly-L-lysine and carboxymethylcellulose. Jpn J Med Sci Biol. Oct. 1990;43(5):171-82.
Kimura et al., Binding of oligoguanylate to scavenger receptors is required for oligonucleotides to augment NK cell activity and induce IFN. J Biochem (Tokyo). Nov. 1994;116(5):991-4.
Klinman et al., CpG motifs present in bacteria DNA rapidly induce lymphocytes to secrete interleukin 6, interleukin 12, and interferon gamma. Proc Natl Acad Sci U S A. Apr. 2, 1996;93(7):2879-83.
Krieg et al., Lymphocyte activation mediated by oligodeoxynucleotides or DNA containing novel un-methylated CpG motifs. American College of Rheumatology 58th National Scientific Meeting. Minneapolis, Minnesota, Oct. 22, 1994. Abstracts. Arthritis Rheum. Sep. 1994;37(9 Suppl).
Krieg et al., Oligodeoxynucleotide modifications determine the magnitude of B cell stimulation by CpG motifs. Antisense Nucleic Acid Drug Dev. 1996 Summer;6(2):133-9.
Krieg et al., Phosphorothioate oligodeoxynucleotides: antisense or anti-protein? Antisense Res Dev. 1995 Winter;5(4):241.
Krieg et al., Leukocyte stimulation by oligodeoxynucleotides. In: Applied Antisense Oligonucleotide Technology. 1998:431-48.
Krieg, CpG DNA: a pathogenic factor in systemic lupus erythematosus? J Clin Immunol. Nov. 1995;15(6):284-92.
Krieg et al., CpG motifs in bacterial DNA trigger direct B-cell activation. Nature. Apr. 6, 1995;374(6522):546-9.
Krieg et al., Modification of antisense phosphodiester oligodeoxynucleotides by a 5' cholesteryl moiety increases cellular association and improves efficacy. Proc Natl Acad Sci U S A. Feb. 1, 1993;90(3):1048-52.

Krieg et al., The role of CpG dinucleotides in DNA vaccines. Trends Microbiol. Jan. 1998;6(1):23-7.

Krieg, An innate immune defense mechanism based on the recognition of CpG motifs in microbial DNA. J Lab Clin Med. Aug. 1996;128(2):128-33.

Krieg et al., Chapter 8: Immune Stimulation by Oligonucleotides. In: Antisense Research and Application. Crooke, Ed. 1998:243-62.

Krieg et al., Bacterial DNA or oligonucleotides containing CpG motifs protect mice from lethal L. monocytogenes challenge. 1996 Meeting on Molecular Approaches to the Control of Infectious Diseases. Cold Spring Harbor Laboratory, Sep. 9-13, 1996: 116.

Krieg et al., The CpG motif: Implications for clinical immunology. BioDrugs. Nov. 1, 1998;10(5):341-6.

Krieg et al., Sequence motifs in adenoviral DNA block immune activation by stimulatory CpG motifs. Proc Natl Acad Sci U S A. Oct. 13, 1998;95(21):12631-6.

Krieg et al., CpG DNA induces sustained IL-12 expression in vivo and resistance to Listeria monocytogenes challenge. J Immunol. Sep. 1, 1998;161(5):2428-34.

Krieg et al., Infection. In: McGraw Hill Book. 1996: 242-3.

Krieg et al., Lymphocyte activation by CpG dinucleotide motifs in prokaryotic DNA. Trends Microbiol. Feb. 1996;4(2):73-6.

Kukowska-Latallo et.al., Efficient transfer of genetic material into mammalian cells using Starburst polyamidoamine dendrimers. Proc Natl Acad Sci U S A. May 14, 1996;93(10):4897-902.

Kuramoto et al., Changes of host cell infiltration into Meth A fibrosarcoma tumor during the course of regression induced by injections of a BCG nucleic acid fraction. Int J Immunopharmacol. Jul. 1992;14(5):773-82.

Kuramoto et al., Oligonucleotide sequences required for natural killer cell activation. Jpn J Cancer Res. Nov. 1992;83(11):1128-31.

Kuramoto et al., In situ infiltration of natural killer-like cells induced by intradermal injection of the nucleic acid fraction from BCG. Microbiol Immunol. 1989;33(11):929-40.

Leibson et al., Role of gamma-interferon in antibody-producing responses. Nature. Jun. 28-Jul. 4, 1984;309(5971):799-801.

Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.

Letsinger et al., Synthesis and properties of modified oligonucleotides. Nucleic Acids Symp Ser. 1991;(24):75-8.

Litzinger et al., Fate of cationic liposomes and their complex with oligonucleotide in vivo. Biochim Biophys Acta. Jun. 11, 1996;1281(2):139-49.

MacKellar et al., Synthesis and physical properties of anti-HIV antisense oligonucleotides bearing terminal lipophilic groups. Nucleic Acids Res. Jul. 11, 1992;20(13):3411-7.

Maloy et al., Induction of Th1 and Th2 CD4+ T cell responses by oral or parenteral immunization with ISCOMS. Eur J Immunol. Oct. 1995;25(10):2835-41.

Messina et al., The influence of DNA structure on the in vitro stimulation of murine lymphocytes by natural and synthetic polynucleotide antigens. Cell Immunol. Mar. 1993;147(1):148-57.

Mojcik et al., Administration of a phosphorothioate oligonucleotide antisense to murine endogenous retroviral MCF env causes immune effects in vivo in a sequence-specific manner. Clin Immunol Immunopathol. May 1993;67(2):130-6.

Pisetsky et al., The immunologic properties of DNA. J Immunol. Jan. 15, 1996;156(2):421-3.

Pisetsky et al., Influence of backbone chemistry on immune activation by synthetic oligonucleotides. Biochem Pharmacol. Dec. 15, 1999;58(12):1981-8.

Pisetsky, Immunologic consequences of nucleic acid therapy. Antisense Res Dev. 1995 Fall;5(3):219-25.

Pisetsky et al., Stimulation of in vitro proliferation of murine lymphocytes by synthetic oligodeoxynucleotides. Mol Biol Rep. Oct. 1993;18(3):217-21.

Rodgers et al., Effects of acute administration of O,S,S-trimethyl phosphorodithioate on the generation of cellular and humoral immune responses following in vitro stimulation. Toxicology. Oct. 1988;51(2-3):241-53.

Sands et al., Biodistribution and metabolism of internally 3H-labeled oligonucleotides. I. Comparison of a phosphodiester and a phosphorothioate. Mol Pharmacol. May 1994;45(5):932-43.

Sato et al., Immunostimulatory DNA sequences necessary for effective intradermal gene immunization. Science. Jul. 19, 1996;273(5273):352-4.

Sjolander et al., Kinetics, localization and isotype profile of antibody responses to immune stimulating complexes (iscoms) containing human influenza virus envelope glycoproteins. Scand J Immunol. Feb. 1996;43(2):164-72.

Sonehara et al., Hexamer palindromic oligonucleotides with 5'-CG-3' motif(s) induce production of interferon. J Interferon Cytokine Res. Oct. 1996;16(10):799-803.

Stein et al., Problems in interpretation of data derived from in vitro and in vivo use of antisense oligodeoxynucleotides. Antisense Res Dev. 1994 Summer;4(2):67-9.

Stein et al., Physicochemical properties of phosphorothioate oligodeoxynucleotides. Nucleic Acids Res. Apr. 25, 1988;16(8):3209-21.

Stein et al., Non-antisense effects of oligodeoxynucleotides. Antisense Technology. 1997; ch11:241-64.

Stirchak et al., Uncharged stereoregular nucleic acid analogs: 2. Morpholino nucleoside oligomers with carbamate internucleoside linkages. Nucleic Acids Res. Aug. 11, 1989;17(15):6129-41.

Tokunaga et al., Synthetic oligonucleotides with particular base sequences from the cDNA encoding proteins of Mycobacterium bovis BCG induce interferons and activate natural killer cells. Microbiol Immunol. 1992;36(1):55-66.

Vanderiessche et al., Acyclic oligonucleotides: possibilities and limitations. Tetrahedron. Aug. 13, 1993;49(33):7223-38.

Vlassov et al., In Vivo pharmocokinetics of oligonucleotides following administration by different routes. CRC Press, Inc. Chapter 5. 1995:71-83.

Whitesell et al., Stability, clearance, and disposition of intraventricularly administered oligodeoxynucleotides: implications for therapeutic application within the central nervous system. Proc Natl Acad Sci U S A. May 15, 1993;90(10):4665-9.

Wu et al., Receptor-mediated gene delivery and expression in vivo. J Biol Chem. Oct. 15, 1988;263(29):14621-4.

Yamamoto et al., Lipofection of synthetic oligodeoxyribonucleotide having a palindromic sequence of AACGTT to murine splenocytes enhances interferon production and natural killer activity. Microbiol Immunol. 1994;38(10):831-6.

Yamamoto et al., Unique palindromic sequences in synthetic oligonucleotides are required to induce IFN [correction of INF] and augment IFN-mediated [correction of IFN] natural killer activity. J Immunol. Jun. 15, 1992;148(12):4072-6.

Yamamoto et al., [Commemorative lecture of receiving Imamura Memorial Prize. II. Mode of action of oligonucleotide fraction extracted from Mycobacterium bovis BCG] Kekkaku. Sep. 1994;69(9):571-4. Japanese.

Yamamoto et al., Ability of oligonucleotides with certain palindromes to induce interferon production and augment natural killer cell activity is associated with their base length. Antisense Res Dev. 1994 Summer;4(2):119-22.

Yamamoto et al., Synthetic oligonucleotides with certain palindromes stimulate interferon production of human peripheral blood lymphocytes in vitro. Jpn J Cancer Res. Aug. 1994;85(8):775-9. Abstract Only.

Yamamoto, Cytokine production inducing action of oligo DNA. Rinsho Meneki. 1997; 29(9): 1178-84. Japanese.

Yi et al., Rapid immune activation by CpG motifs in bacterial DNA. Systemic induction of IL-6 transcription through an antioxidant-sensitive pathway. J Immunol. Dec. 15, 1996;157(12):5394-402.

Yi et al., IFN-gamma promotes IL-6 and IgM secretion in response to CpG motifs in bacterial DNA and oligodeoxynucleotides. J Immunol. Jan. 15, 1996;156(2):558-64.

Zhao et al., Modulation of oligonucleotide-induced immune stimulation by cyclodextrin analogs. Biochem Pharmacol. Nov. 22, 1996;52(10):1537-44.

Zhao et al., Effect of different chemically modified oligodeoxynucleotides on immune stimulation. Biochem Pharmacol. Jan. 26, 1996;51(2):173-82.

Patent Interference No. 105,171. Iowa Preliminary Motion 3 (for judgment based on failure to comply with 35 U.S.C. 135(b)). (Electronically filed, unsigned). Jun. 7, 2004.
Patent Interference No. 105,171. Iowa Preliminary Motion 4 (for judgment of no interference in fact). (Electronically filed, unsigned). Jun. 7, 2004.
Patent Interference No. 105,171. Iowa Preliminary Motion 5 (for judgment based on lack of enablement). (Electronically filed, unsigned). Jun. 7, 2004.
Patent Interference No. 105,171. Iowa Preliminary Motion 6 (for judgment based on lack of adequate written description). (Electronically filed, unsigned). Jun. 7, 2004.
Patent Interference No. 105,171. Iowa Preliminary Motion 7 (motion to redefine interference to designate claims as not corresponding to the Count). (Electronically filed, unsigned). Jun. 7, 2004.
Patent Interference No. 105,171. Iowa Preliminary Motion 8 (contingent motion to redefine the Count). (Electronically filed, unsigned). Jun. 7, 2004.
Patent Interference No. 105,171. Iowa Preliminary Motion 9 (motion for benefit of earlier application). (Electronically filed, unsigned). Jun. 7, 2004.
Patent Interference No. 105,171. Iowa Preliminary Motion 10 (contingent motion to redefine the interference by adding a continuation application). (Electronically filed, unsigned). Jul. 2, 2004.
Patent Interference No. 105,171. Regents of the University of California Opposition 3 (to Iowa Preliminary Motion 3 for judgment under 35 USC 135(b)). Sep. 9, 2004.
Patent Interference No. 105,171. Regents of the University of California Opposition 4 (to Iowa Preliminary Motion 4 for judgment of no interference in fact). Sep. 9, 2004.
Patent Interference No. 105,171. Regents of the University of California Opposition 5 (to Iowa Preliminary Motion 5 for judgment that UC's claim is not enabled). Sep. 9, 2004.
Patent Interference No. 105,171. Regents of the University of California Opposition 6 (to Iowa Preliminary Motion 6 for judgment based on lack of adequate written description). Sep. 9, 2004.
Patent Interference No. 105,171. Regents of the University of California Opposition 7 (to Iowa Preliminary Motion 7 to redefine the interference). Sep. 9, 2004.
Patent Interference No. 105,171. Regents of the University of California Opposition 8 (to Iowa Preliminary Motion 8 to redefine the Count). Sep. 9, 2004.
Patent Interference No. 105,171. Regents of the University of California Response 9 (to Iowa Contingent Motion 9 for benefit). Sep. 9, 2004.
Patent Interference No. 105,171. Regents of the University of California Opposition 10 (to Iowa Contingent Motion 10 to redefine the interference). Sep. 9, 2004.
Patent Interference No. 105,171. Regents of the University of California Opposition 11 (to Iowa Contingent Motion 11 to suppress). Oct. 15, 2004.
Patent Interference No. 105,171. Iowa Reply 3 (in support of Iowa Preliminary Motion 3 for judgment under 35 U.S.C. §135(b)) (Electronically filed, unsigned). Oct. 15, 2004.
Patent Interference No. 105,171. Iowa Reply 4 (in support of Iowa Preliminary Motion for judgment of no interference in fact) (Electronically filed, unsigned). Oct. 15, 2004.
Patent Interference No. 105,171. Iowa Reply 5 (in support of Iowa Preliminary Motion 5 for judgment that UC's claim 205 is not enabled) (Electronically filed, unsigned). Oct. 15, 2004.
Patent Interference No. 105,171. Iowa Reply 6 (in support of Iowa Preliminary Motion 6 for judgment based on lack of adequate written description) (Electronically filed, unsigned). Oct. 15, 2004.
Patent Interference No. 105,171. Iowa Reply 7 (in support of Iowa Preliminary Motion 7 to redefine the interference) (Electronically filed, unsigned). Oct. 15, 2004.
Patent Interference No. 105,171. Iowa Reply 8 (in support of Iowa Preliminary Motion 8 to redefine the count) (Electronically filed, unsigned). Oct. 15, 2004.
Patent Interference No. 105,171. Iowa Reply 10 (in support of Iowa Preliminary Motion 10 to redefine the interference) (Electronically filed, unsigned). Oct. 15, 2004.
Patent Interference No. 105,171. Iowa Reply 11 (in support of Iowa Miscellaneous Motion to suppress). (Electronically filed, unsigned). Oct. 18, 2004.
Patent Interference No. 105,171. Regents of the University of California Preliminary Statement. Jun. 7, 2004.
Patent Interference No. 105,171. Regents of the University of California Preliminary Motion 1 (to designate additional claims of Iowa patent as corresponding to the Count). Jun. 7, 2004.
Patent Interference No. 105,171. Regents of the University of California Preliminary Motion 2 (for judgment based on lack of written description support and introducing new matter). Jun. 7, 2004.
Patent Interference No. 105,171. Regents of the University of California Preliminary Motion 3 (for judgment based on anticipation). Jun. 7, 2004.
Patent Interference No. 105,171. Regents of the University of California Preliminary Motion 4 (for judgment based on obviousness). Jun. 7, 2004.
Patent Interference No. 105,171. Regents of the University of California Preliminary Motion 5 (for judgment based on anticipation). Jun. 7, 2004.
Patent Interference No. 105,171. Regents of the University of California Preliminary Motion 6 (for judgment based on inequitable conduct). Jun. 7, 2004.
Patent Interference No. 105,171. Regents of the University of California Contingent Preliminary Motion 7 (for benefit of an earlier application under 37 CFR 1.633(j)). Jul. 2, 2004.
Patent Interference No. 105,171. Regents of the University of California Contingent Preliminary Motion 8 (to add additional claims under 37 CFR 1.633(c)(2) and (i)). Jul. 2, 2004.
Amended Claims for U.S. Appl. No. 09/265,191, filed Mar. 10, 1999.
Patent Interference No. 105,171. Iowa Opposition 1 (opposition to motion to designate additional claims as corresponding to the Count) (Electronically filed, unsigned). Sep. 9, 2004.
Patent Interference No. 105,171. Iowa Opposition 2 (opposition to motion for judgment based on lack of written description support and introducing new matter) (Electronically filed, unsigned). Sep. 9, 2004.
Patent Interference No. 105,171. Iowa Opposition 3 (opposition to motion for judgment based on anticipation) (Electronically filed, unsigned). Sep. 9, 2004.
Patent Interference No. 105,171. Iowa Opposition 4 (opposition to motion for judgment based on obviousness) (Electronically filed, unsigned). Sep. 9, 2004.
Patent Interference No. 105,171. Iowa Opposition 5 (opposition to motion for judgment based on anticipation) (Electronically filed, unsigned). Sep. 9, 2004.
Patent Interference No. 105,171. Iowa Opposition 6 (opposition to motion for judgment based on inequitable conduct) (Electronically filed, unsigned). Sep. 9, 2004.
Patent Interference No. 105,171. Iowa Opposition 7 (opposition to motion for benefit of an earlier application under 7 CFR 1.633(j)) (Electronically filed, unsigned). Sep. 9, 2004.
Patent Interference No. 105,171. Iowa Opposition 8 (opposition to motion to add additional claims under 37 CFR 1.633 (2) and (i)) (Electronically filed, unsigned). Sep. 9, 2004.
Patent Interference No. 105,171. Regents of the University of California Reply 1 (to Iowa's opposition to UC's motion to designate Iowa claims as corresponding to the Count). Oct. 15, 2004.
Patent Interference No. 105,171. Regents of the University of California Reply 2 (to Iowa's opposition to UC Preliminary Motion 2 for Judgment). Oct. 15, 2004.
Patent Interference No. 105,171. Regents of the University of California Reply 3 (to Iowa's Opposition to UC Preliminary Motion 3 for Judgment). Oct. 15, 2004.
Patent Interference No. 105,171. Regents of the University of California Reply 4 (to Iowa's Opposition to UC Preliminary Motion 4 for Judgment). Oct. 15, 2004.
Patent Interference No. 105,171. Regents of the University of California Reply 5 (to Iowa's Opposition to UC Preliminary Motion 5 for Judgment). Oct. 15, 2004.
Patent Interference No. 105,171. Regents of the University of California Reply 6 (to Iowa's opposition to UC Preliminary Motion 6 for judgment). Oct. 15, 2004.

Patent Interference No. 105,171. Regents of the University of California Reply 7 (to Iowa's Opposition to UC Preliminary Motion 7 for Benefit). Oct. 15, 2004.
Patent Interference No. 105,171. Regents of the University of California Reply 8 (to Iowa's Opposition to UC Preliminary Motion 8 to add additional claims). Oct. 15, 2004.
Patent Interference No. 105,171. Decision on Motion under 37 CFR §41.125. Mar. 10, 2005.
Patent Interference No. 105,171. Judgment and Order. Mar. 10, 2005.
Patent Interference No. 105,171. Regents of the University of California. Brief of Appellant. Jul. 5, 2005.
Patent Interference No. 105,171. University of Iowa and Coley Pharmaceutical Group, Inc. Brief of Appellees. Aug. 17, 2005.
Patent Interference No. 105,171. Regents of the University of California. Reply Brief of Appellant. Sep. 6, 2005.
Patent Interference No. 105,171. Regents of the University of California. Decision of CAFC. Jul. 17, 2006.
Bennett, Intracellular delivery of oligonucleotides with cationic liposomes. In: Delivery Strategies for Antisense Oligonucleotide Therapeutics. Akthar, Ed. 1995:223-32.
Press Release, Jan. 2007, "Coley Pharmaceutical Group Updates Hepatitis C Drug Development Strategy".
Press Release, Jun. 2007, "Coley Pharmaceutical Group Announces Pfizer's Discontinuation of Clinical Trials for PF-3512676 Combined with Cytotoxic Chemotherapy in Advanced Non Small Cell Lung Cancer".
Patent Interference No. 105,526. Krieg Substantive Motion 1 (for unpatentability based on interference estoppel). (Electronically filed, unsigned).
Patent Interference No. 105,526.. Krieg Substantive Motion 2 (for judgment based on inadequate written description and/or enablement). (Electronically filed, unsigned). Jun. 18, 2007.
Patent Interference No. 105,526. Krieg Contingent Responsive Motion (to add new claims 104 and 105). (Electronically filed, unsigned). Jul. 25, 2007.
Patent Interference No. 105,526. Krieg Substantive Motion 3 (for judgment based on prior art). (Electronically filed, unsigned). Jun. 18, 2007.
Patent Interference No. 105,526. Raz Motion 1 (Unpatentability of Krieg Claims under 35 U.S.C. § 112, First Paragraph). (Electronically filed, unsigned). Jun. 18, 2007.
Patent Interference No. 105,526. Raz Motion 2 (Raising a Threshold Issue of no. Interference-inFact). (Electronically filed, unsigned). Jun. 18, 2007.
Patent Interference No. 105,526.. Raz Motion 3 (Krieg's Claims are Unpatentable Over Prior Art Under 35 U.S.C. § 102(b)) (Electronically filed, unsigned). Jun. 18, 2007.
Patent Interference No. 105,526. Raz Motion 4 (To Designate Krieg Claims 46 and 82-84 as Corresponding to Count 1). (Electronically filed, unsigned). Jun. 18, 2007.
Patent Interference No. 105,526. Raz Responsive Miscellaneous Motion 5 (to revive the Raz Parent Application) (Electronically filed, unsigned) Jul. 25, 2007.
Patent Interference No. 105,526. Raz Contingent Responsive Motion 6 (To Add a New Claim 58) (Electronically filed, unsigned) Jul. 25, 2007.
Patent Interference No. 105,526. Krieg Opposition 1 (Opposition to Motion for Lack of Enablement and Written Description) (Electronically filed, unsigned) Sep. 10, 2007.
Patent Interference No. 105,526. Krieg Opposition 2 (To Raz Motion 2) (Electronically filed, unsigned) Sep. 10, 2007.
Patent Interference No. 105,526. Krieg Opposition 3 (To Raz Motion 3) (Electronically filed, unsiged) Sep. 10, 2007.
Patent Interference No. 105,526. Krieg Opposition 4 (Opposition to Motion for Designating Claims 46 and 82-84 as Corresponding to the Court) (Electronically filed, unsigned) Sep. 10, 2007.
Patent Interference No. 105,526. Krieg Opposition 6 (Opposition to Raz Contingent Responsive Motion 6) (Electronically filed, unsigned) Sep. 10, 2007.
Patent Interference No. 105,526. Raz Opposition 1 (Opposing Krieg Substantive Motion 1) (Electronically filed, unsigned) Sep. 10, 2007.
Patent Interference No. 105,526. Raz Opposition 2 (Opposing Krieg Substantive Motion 2) (Electronically filed, unsigned) Sep. 10, 2007.
Patent Interference No. 105,526. Raz Opposition 4 (Opposing Krieg Contingent Responsive Motion to Add New Claims 104 and 105) (Electronically filed, unsigned) Sep. 10, 2007.
Patent Interference No. 105,526. Krieg Reply 1 (Reply to Raz opposition 1) Oct. 5, 2007.
Patent Interference No. 105,526. Krieg Reply 2 (Reply to Raz opposition 2) Oct. 5, 2007.
Patent Interference No. 105,526. Krieg Reply 4 (Reply to Raz opposition 4) Oct. 5, 2007.
Patent Interference No. 105,526. Raz Reply 1 (Reply to Krieg opposition 1) Oct. 5, 2007.
Patent Interference No. 105,526. Raz Reply 2 (Reply to Krieg opposition 2) Oct. 5, 2007.
Patent Interference No. 105,526. Raz Reply 3 (Reply to Krieg opposition 3) Oct. 5, 2007.
Patent Interference No. 105,526. Raz Reply 4 (Reply to Krieg opposition 4) Oct. 5, 2007.
Patent Interference No. 105,526. Raz Reply 6 (Reply to Krieg opposition 6) Oct. 5, 2007.

* cited by examiner

IMMUNOMODULATORY OLIGONUCLEOTIDES

RELATED APPLICATIONS

This application is a continuation of U.S. patent application Ser. No. 10/690,495 filed on Oct. 21, 2003 and now which a continuation of U.S. patent application Ser. No. 09/415,142, filed Oct. 9, 1999, now abandoned, which is a divisional of U.S. patent application Ser. No. 08/386,063, filed Feb. 7, 1995, now issued as U.S. Pat. No. 6,194,388 B1, which is a continuation-in-part of U.S. patent application Ser. No. 08/276,358, filed Jul. 15, 1994, now abandoned.

GOVERNMENT SUPPORT

The work resulting in this invention was supported in part by National Institute of Health Grant No. R29-AR42556-01. The U.S. Government has certain rights in the invention.

BACKGROUND OF THE INVENTION

DNA Binds to Cell Membrane and is Internalized

In the 1970's, several investigators reported the binding of high molecular weight DNA to cell membranes (Lerner, R. A., W. Meinke, and D. A. Goldstein. 1971. "Membrane-associated DNA in the cytoplasm of diploid human lymphocytes". *Proc. Natl. Acad. Sci. USA* 68:1212; Agrawal, S. K, R. W. Wagner, P. K. McAllister, and B. Rosenberg. 1975. "Cell-surface-associated nucleic acid in tumorigenic cells made visible with platinum-pyrimidine complexes by electron microscopy". *Proc. Nat. Acad. Sci. USA* 72:928). In 1985 Bennett et al. presented the first evidence that DNA binding to lymphocytes is similar to a ligand receptor interaction: binding is saturable, competitive, and leads to DNA endocytosis and degradation (Bennett, R. M., G. T. Gabor, and M. M. Merritt, 1985. "DNA binding to human leukocytes. Evidence for a receptor-mediated association, internalization, and degradation of DNA". *J Clin. Invest.* 76:2182). Like DNA, oligodeoxyribonucleotides (ODNs) are able to enter cells in a saturable, sequence independent, and temperature and energy dependent fashion (reviewed in Jaroszewski, J. W., and J. S. Cohen. 1991. "Cellular uptake of antisense oligodeoxynucleotides". *Advanced Drug Delivery Reviews* 6:235; Akhtar, S., Y. Shoji, and R. L. Juliano. 1992. "Pharmaceutical aspects of the biological stability and membrane transport characteristics of antisense oligonucleotides". In: *Gene Regulation: Biology of Antisense RNA and DNA*. R. P. Erickson, and J. G. Izant, eds. Raven Press, Ltd. New York, pp. 133; and Zhao, Q., T. Waldschimdt, E. Fisher, C. J. Herrera, and A. M. Krieg., 1994. "Stage specific oligonucleotide uptake in murine bone marrow B cell precursors". *Blood*, 84:3660). No receptor for DNA or ODN uptake has yet been cloned, and it is not yet clear whether ODN binding and cell uptake occurs through the same or a different mechanism from that of high molecular weight DNA.

Lymphocyte ODN uptake has been shown to be regulated by cell activation. Spleen cells stimulated with the B cell mitogen LPS had dramatically enhanced ODN uptake in the B cell population, while spleen cells treated with the T cell mitogen Con A showed enhanced ODN uptake by T but not B cells (Krieg, A. M., F. Grnelig-Meyling, M. F. Gourley, W. J. Kisch, L. A. Chrisey, and A. D. Steinberg. 1991. "Uptake of oligodeoxyribonucleotides by lymphoid cells is heterogeneous and inducible". *Antisense Research and Development* 1:161).

Immune Effects of Nucleic Acids

Several polynucleotides have been extensively evaluated as biological response modifiers. Perhaps the best example is poly (I,C) which is a potent inducer of IFN production as well as a macrophage activator and inducer of NK activity (Talmadge, J. E., J. Adams, H. Phillips, M. Collins, B. Lenz, M. Schneider, E. Schlick, R. Ruffmann, R. H. Wiltrout, and M. A. Chirigos. 1985. "Immunomodulatory effects in mice of polyinosinic-polycytidylic acid complexed with poly-L:-lysine and carboxymethylcellulose". *Cancer Res.* 45:1058; Wiltrout, R. H., R. R. Salup, T. A. Twilley, and J. E. Talmadge. 1985. "Immunomodulation of natural killer activity by polyribonucleotides". *J. Biol. Resp. Mod* 4:512; Krown, S. E. 1986. "Interferons and interferon inducers in cancer treatment". *Sem. Oncol.* 13:207; and Ewel, C. H., S. J. Urba, W. C. Kopp, J. W. Smith II, PG. Steis, J. L. Rossio, D. L. Longo, M. J. Jones, W. G. Alvord, C. M. Pinsky, J. M. Beveridge, K. L. McNitt, and S. P. Creekmore. 1992. "Polyinosinic-polycytidylic acid complexed with poly-L-lysine and carboxymethylcellulose in combination with interleukin 2 in patients with cancer: clinical and immunological effects". *Canc. Res.* 52:3005). It appears that this murine NK activation may be due solely to induction of IFN β secretion (Ishikawa, R., and C. A. Biron. 1993. "IFN induction and associated changes in splenic leukocyte distribution". *J. Immunol.* 150:3713). This activation was specific for the ribose sugar since deoxyribose was ineffective. Its potent in vitro antitumor activity led to several clinical trials using poly (I,C) complexed with poly-L-lysine and carboxymethylcellulose (to reduce degradation by RNAse) (Talmadge, J. E., et al., 1985. cited supra; Wiltrout, R. H., et al., 1985. cited supra); Krown, S. E., 1986. cited supra); and Ewel, C. H., et al. 1992. cited supra). Unfortunately, toxic side effects have thus far prevented poly (I,C) from becoming a useful therapeutic agent.

Guanine ribonucleotides substituted at the C8 position with either a bromine or a thiol group are B cell mitogens and may replace "B cell differentiation factors" (Feldbush, T. L., and Z. K. Ballas. 1985. "Lymphokine-like activity of 8-mercaptoguanosine: induction of T and B cell differentiation". *J. Immunol.* 134:3204; and Goodman, M. G. 1986. "Mechanism of synergy between T cell signals and C8-substituted guanine nucleosides in humoral immunity: B lymphotropic cytokines induce responsiveness to 8-mercaptoguanosine". *J. Immunol.* 136:3335). 8-mercaptoguanosine and 8-bromo-guanosine also can substitute for the cytokine requirement for the generation of MHC restricted CT1 (Feldbush, T. L., 1985. cited supra), augment murine NK activity (Koo, G. C., M. E. Jewell, C. L. Manyak, N. H. Sigal, and L. S. Wicker. 1988. "Activation of murine natural killer cells and macrophages by 8-bromoguanosine". *J. Immunol.* 140:3249), and synergize with IL-2 in inducing murine LAK generation (Thompson, R. A., and Z. K. Ballas. 1990. "Lymphokine-activated killer (LAK) cells. V. 8-Mercaptoguanosine as an IL-2-sparing agent in LAK generation". *J. Immunol.* 145:3524). The NK and LAK augmenting activities of these C8-substituted guanosines appear to be due to their induction of IFN (Thompson, R. A., et al. 1990. cited supra). Recently, a 5' triphosphorylated thymidine produced by a mycobacterium was found to be mitogenic for a subset of human γδ T cells (Constant, P., F. Davodeau, M. -A. Peyrat, Y. Poquet, G. Puzo, M. Bonneville, and J. -J. Fournie. 1994. "Stimulation of human γε T cells by nonpeptidic mycobacterial ligands" *Science* 264:267). This report indicated the possibility that the immune system may have evolved ways to preferentially respond to microbial nucleic acids.

Several observations suggest that certain DNA structures may also have the potential to activate lymphocytes. For example, Bell et al. reported that nucleosomal protein-DNA complexes (but not naked DNA) in spleen cell supernatants caused B cell proliferation and immunoglobulin secretion (Bell, D. A., B. Morrison, and P. VandenBygaart. 1990. "Immunogenic DNA-related factors". *J. Clin. Invest.* 85:1487). In other cases, naked DNA has been reported to have immune effects. For example, Messina et al. have recently reported that 260 to 800 bp fragments of poly (dG)• (dC) and poly (dG•dC) were mitogenic for B cells (Messina, J. P., G. S. Gilkeson, and D. S. Pisetsky. 1993. "The influence of DNA structure on the in vitro stimulation of murine lymphocytes by natural and synthetic polynucleotide antigens". *Cell. Immunol.* 147:148). Tokunaga, et al. have reported that dGe dC induces γ-IFN and NK activity (Tokunaga, S. Yamamoto, and K Namba. 1988. "A synthetic single-stranded DNA, poly(dG,dC), induces interferon-α/β and -γ, augments natural killer activity, and suppresses tumor growth" *Jpn. J Cancer Res.* 79:682). Aside from such artificial homopolymer sequences, Pisetsky et al. reported that pure mammalian DNA has no detectable immune effects, but that DNA from certain bacteria induces B cell activation and immunoglobulin secretion (Messina, J. P., G. S. Gilkeson, and D. S. Pisetsky. 1991. "Stimulation of in vitro murine lymphocyte proliferation by bacterial DNA". *J. Immunol.* 147:1759). Assuming that these data did not result from some unusual contaminant, these studies suggested that a particular structure or other characteristic of bacterial DNA renders it capable of triggering B cell activation. Investigations of mycobacterial DNA sequences have demonstrated that ODN which contain certain palindrome sequences can activate NK cells (Yanamoto, S., T. Yamamoto, T. Kataoka, E. Kuramoto, O. Yano, and T. Tokunaga. 1992. "Unique palindromic sequences in synthetic oligonucleotides are required to induce INF and augment INF-mediated natural killer activity". *J. Immunol.* 148:4072; Kuramoto, E., O. Yano, Y. Kimura, M. Baba, T. Makino, S. Yamamoto, T. Yamamoto, T. Kataoka, and T. Tokunaga 1992. "Oligonucleotide sequences required for natural killer cell activation". *Jpn. J Cancer Res.* 83:1128).

Several phosphorothioate modified ODN have been reported to induce in vitro or in vivo B cell stimulation (Tanaka, T., C. C. Chu, and W. E. Paul. 1992. "An antisense oligonucleotide complementary to a sequence in Iγ2b increases γ2b germline transcripts, stimulates B cell DNA synthesis, and inhibits immunoglobulin secretion". *J. Exp. Med* 175:597; Branda, R. F., A. L. Moore, L. Mathews, J. J. McCormack, and G. Zon. 1993. "Immune stimulation by an antisense oligomer complementary to the rev gene of HIV-1". *Biochem. Pharmacol.* 45:2037; McIntyre, K. W., K Lombard-Gillooly, J. R Perez, C. Kunsch, U. M. Sarmiento, J. D. Larigan, K. T. Landreth, and R Narayanarn 1993. "A sense phosphorothioate oligonucleotide directed to the initiation codon of transcription factor NF-κ β T65 causes sequence-specific immune stimulation". *Antisense Res. Develop.* 3:309; and Pisetsky, D. S., and C. F. Reich 1993. "Stimulation of murine lymphocyte proliferation by a phosphorothioate oligonucleotide with antisense activity for herpes simplex virus". *Life Sciences* 54:101). These reports do not suggest a common structural motif or sequence element in these ODN that might explain their effects.

The CREB/ATF Family of Transcription Factors and their Role in Replication

The cAMP response element binding protein (CREB) and activating transcription factor (ATF) or CREB/ATF family of transcription factors is a ubiquitously expressed class of transcription factors of which 11 members have so far been cloned (reviewed in de Groot, R. P., and P. Sassone-Corsi: "Hormonal control of gene expression: Multiplicity and versatility of cyclic adenosine 3',5'-monophosphate-responsive nuclear regulators". *Mol. Endocrin.* 7:145, 1993; Lee, K. A. W., and N. Masson: "Transcriptional regulation by CREB and its relatives". *Biochim Biophys. Acta* 1174:221, 1993.). They all belong to the basic region/leucine zipper (bZip) class of proteins. All cells appear to express one or more CREB/ATF proteins, but the members expressed and the regulation of mRNA splicing appear to be tissue-specific. Differential splicing of activation domains can determine whether a particular CREB/ATF protein will be a transcriptional inhibitor or activator. Many CREB/ATF proteins activate viral transcription, but some splicing variants which lack the activation domain are inhibitory. CREB/ATF proteins can bind DNA as homo- or hetero- dimers through the cAMP response element, the CRE, the consensus form of which is the unmethylated sequence TGACGTC (binding is abolished if the CpG is methylated) (Iguchi-Ariga, S. M. M., and W. Schaffner: "CpG methylation of the cAMP-responsive enhancer/promoter sequence TGACGTCA abolishes specific factor binding as well as transcriptional activation". *Genes & Develop.* 3:612, 1989.).

The transcriptional activity of the CRE is increased during B cell activation (Xie, H. T. C. Chiles, and T. L. Rothstein: "Induction of CREB activity via the surface Ig receptor of B cells". *J. Immunol.* 151:880, 1993.). CREB/ATF proteins appear to regulate the expression of multiple genes through the CRE including immunologically important genes such as fos, jun B, Rb-1, IL-6, IL-1 (Tsukada, J., K. Saito, W. R. Waterman, A. C. Webb, and P. E. Auron: "Transcription factors NF-IL6 and CREB recognize a common essential site in the human prointerleukin 1β gene". *Mol. Cell. Biol.* 14:7285, 1994; Gray, G. D., O. M. Hernandez, D. Hebel, M. Root, J. M. Pow-Sang, and E. Wickstrom: "Antisense DNA inhibition of tumor growth induced by c-Ha-ras oncogene in nude mice". *Cancer Res.* 53:577, 1993), IFN-β (Du, W., and T. Maniatis: "An ATF/CREB binding site protein is required for virus induction of the human interferon B gene". *Proc. Natl. Acad. Sci. USA* 89:2150, 1992), TGF-β1(Asiedu, C. K., L. Scott, R. K. Assoian, M. Ehrlich: "Binding of AP-1/CREB proteins and of MDBP to contiguous sites downstream of the human TGF-B 1 gene". *Biochim. Biophys. Acta* 1219:55, 1994.), TGF-β2, class II MHC (Cox, P. M., and C. R. Goding: "An ATF/CREB binding motif is required for aberrant constitutive expression of the MHC class II DRa promoter and activation by SV40 T-antigen". *Nucl. Acids Res.* 20:4881, 1992.), E-selectin, GM-CSF, CD-8α, the germline Igα constant region gene, the TCR Vβ gene, and the proliferating cell nuclear antigen (Huang, D., P. M. Shipman-Appasamy, D. J. Orten, S. H. Hinrichs, and M. B. Prystowsky: "Promoter activity of the proliferating-cell nuclear antigen gene is associated with inducible CRE-binding proteins in interleukin 2-stimulated T lymphocytes". *Mol. Cell. Biol.* 14:4233, 1994.). In addition to activation through the cAMP pathway, CREB can also mediate transcriptional responses to changes in intracellular Ca$^{++}$ concentration (Sheng, M., G. McFadden, and M. E. Greenberg: "Membrane depolarization and calcium induce c-fos transcription via phosphorylation of transcription factor CREB". *Neuron* 4:571, 1990).

The role of protein-protein interactions in transcriptional activation by CREB/ATF proteins appears to be extremely important. Activation of CREB through the cyclic AMP pathway requires protein kinase A (PKA), which phosphorylates CREB$^{341}$ on ser$^{133}$ and allows it to bind to a recently cloned protein, CBP (Kwok, R. P. S., J. R. Lundblad, J. C. Chrivia, J. P. Richards, H. P. Bachinger, R. G. Brennan, S. G. E. Roberts, M. R Green, and R. H. Goodman: "Nuclear protein CBP is a coactivator for the transcription factor CREB". *Nature* 370: 223, 1994; Arias, J., A. S. Alberts, P. Brindle, F. X. Claret, T. Smea, M. Karin, J. Feramisco, and M. Montminy: "Activation of cAMP and mitogen responsive genes relies on a common nuclear factor". *Nature* 370:226, 1994.). CBP in turn interacts with the basal transcription factor TFIIB causing increased transcription. CREB also has been reported to interact with dTAFII 110, a TATA binding protein-associated factor whose binding may regulate transcription (Ferreri, K., G. Gill, and M. Montminy: "The cAMP-regulated transcription factor CREB interacts with a component of the TFIID complex". *Proc. Natl. Acad. Sci. USA* 91:1210, 1994.). In addition to these interactions, CREB/ATF proteins can specifically bind multiple other nuclear factors (Hoeffler, J. P., J. W. Lustbader, and C. -Y. Chen: "Identification of multiple nuclear factors that interact with cyclic adenosine 3',5'-monophosphate response element-binding protein and activating transcription factor-2 by protein-protein interactions". *Mol. Endocrinol.* 5:256, 1991) but the biologic significance of most of these interactions is unknown. CREB is normally thought to bind DNA either as a homodimer or as a heterodimer with several other proteins. Surprisingly, CREB monomers constitutively activate transcription (Krajewski, W., and K. A. W. Lee: "A monomeric derivative of the cellular transcription factor CREB functions as a constitutive activator". *Mol. Cell Biol.* 14:7204, 1994.).

Aside from their critical role in regulating cellular transcription, it has recently been shown that CREB/ATF proteins are subverted by some infectious viruses and retroviruses, which require them for viral replication. For example, the cytomegalovirus immediate early promoter, one of the strongest known mammalian promoters, contains eleven copies of the CRE which are essential for promoter function (Chang, Y. -N., S. Crawford, J. Stall, D. R Rawlins, K. -T. Jeang, and G. S. Hayward: "The palindromic series I repeats in the simian cytomegalovirus major immediate-early promoter behave as both strong basal enhancers and cyclic AMP response elements". *J. Virol.* 64:264, 1990). At least some of the transcriptional activating effects of the adenovirus E1A protein, which induces many promoters, are due to its binding to the DNA binding domain of the CREB/ATF protein, ATF-2, which mediates E1A inducible transcription activation (Liu, F., and M. P Green: "Promoter targeting by adenovirus E1a through interaction with different cellular DNA-binding domains". *Nature* 368:520, 1994). It has also been suggested that E1A binds to the CREB-binding protein, CBP (Arany, Z., W. R. Sellers, D. M. Livingston, and R. Eckner: "E1A-associated p300 and CREB-associated CBP belong to a conserved family of coactivators". *Cell* 77:799, 1994). Human T lymphotropic virus-I (HTLV-1), the retrovirus which causes human T cell leukemia and tropical spastic paresis, also requires CREB/ATF proteins for replication. In this case, the retrovirus produces a protein, Tax, which binds to CREB/ATF proteins and redirects them from their normal cellular binding sites to different DNA sequences (flanked by G- and C-rich sequences) present within the HTLV transcriptional enhancer (Paca-Uccaralertkun, S., L. -J. Zhao, N. Adya, J. V. Cross, B. R Cullen, I. M. Boros, and C.-Z. Giam: "In vitro selection of DNA elements highly responsive to the human T-cell lymphotropic virus type I transcriptional activator, Tax". *Mol. Cell. Biol.* 14:456, 1994; Adya, N., L. -J. Zhao, W. Huang, I. Boros, and C. -Z. Giam: "Expansion of CREB's DNA recognition specificity by Tax results from interaction with Ala-Ala-Arg at positions 282-284 near the conserved DNA-binding domain of CREB". *Proc. Natl. Acad. Sci. USA* 91:5642, 1994).

SUMMARY OF THE INVENTION

The instant invention is based on the finding that certain oligonucleotides containing unmethylated cytosine-guanine (CpG) dinucleotides activate lymphocytes as evidenced by in vitro and in vivo data. Based on this finding, the invention features, in one aspect, novel immunostimulatory oligonucleotide compositions.

In a preferred embodiment, an immunostimulatory oligonucleotide is synthetic, between 2 to 100 base pairs in size and contains a consensus mitogenic CpG motif represented by the formula:

$5'X_1X_2CGX_3X_4 3'$ wherein C and G are unmethylated, $X_1$, $X_2$, $X_3$ and $X_4$ are nucleotides and a GCG trinucleotide sequence is not present at or near the 5' and 3' termini.

For facilitating uptake into cells, CpG containing immunostimulatory oligonucleotides are preferably in the range of 8 to 40 base pairs in size. Prolonged immunostimulation can be obtained using stabilized oligonucleotides, particularly phosphorothioate stabilized oligonucleotides. Enhanced immunostimulatory activity has been observed where $X_1X_2$ is the dinucleotide GpA and/or $X_3X_4$ is the dinucleotide is most preferably TpC or also TpT. Further enhanced immunostimulatory activity has been observed where the consensus motif $X_1X_2CGX_3X_4$ is preceded on the 5' end by a T.

In a second aspect, the invention features useful methods, which are based on the immunostimulatory activity of the oligonucleotides. For example, lymphocytes can either be obtained from a subject and stimulated ex vivo upon contact with an appropriate oligonucleotide; or a non-methylated CpG containing oligonucleotide can be administered to a subject to facilitate in vivo activation of a subject's lymphocytes. Activated lymphocytes, stimulated by the methods described herein (e.g. either ex vivo or in vivo), can boost a subject's immune response. The immunostimulatory oligonucleotides can therefore be used to treat, prevent or ameliorate an immune system deficiency (e.g., a tumor or cancer or a viral, fungal, bacterial or parasitic infection in a subject. In addition, immunostimulatory oligonucleotides can also be administered as a vaccine adjuvant, to stimulate a subject's response to a vaccine. Further, the ability of immunostimulatory cells to induce leukemic cells to enter the cell cycle, suggests a utility for treating leukemia by increasing the sensitivity of chronic leukemia cells and then administering conventional ablative chemotherapy.

In a third aspect, the invention features neutral oligonucleotides (i.e. oligonucleotide that do not contain an unmethylated CpG or which contain a methylated CpG dinucleotide). In a preferred embodiment, a neutralizing oligonucleotide is complementary to an immunostimulatory sequence, but contains a methylated instead of an unmethylated CpG dinucleotide sequence and therefore can compete for binding with unmethylated CpG containing oligonucleotides. In a preferred embodiment, the methylation occurs at one or more of the four carbons and two nitrogens comprising the cytosine six member ring or at one or more of the five carbons and four nitrogens comprising the guanine nine member double ring. 5' methyl cytosine is a preferred methylated CpG.

In a fourth aspect, the invention features useful methods using the neutral oligonucleotides. For example, in vivo administration of neutral oligonucleotides should prove useful for treating diseases such as systemic lupus erythematosus, sepsis and autoimmune diseases, which are caused or exacerbated by the presence of unmethylated CpG dimers in a subject In addition, methylation CpG containing antisense oligonucleotides or oligonucleotide probes would not initiate an immune reaction when administered to a subject in vivo and therefore would be safer than corresponding unmethylated oligonucleotides.

In a fifth aspect, the invention features immunoinhibitory oligonucleotides, which are capable of interfering with the activity of viral or cellular transcription factors. In a preferred embodiment, immunoinhibitory oligonucleotides are between 2to 100 base pairs in size and contain a consensus immunoinhibitory CpG motif represented by the formula:

wherein X=a nucleotide and n=in the range of 0-50. In a preferred embodiment, X is a pyrimidine.

For facilitating uptake into cells, immunoinhibitory oligonucleotides are preferably in the range of 8 to 40 base pairs in size. Prolonged immunostimulation can be obtained using stabilized oligonucleotides, particularly phosphorothioate stabilized oligonucleotides.

In a sixth and final aspect, the invention features various uses for immunoinhibitory oligonucleotides. Immunoinhibitory oligonucleotides have antiviral activity, independent of any antisense effect due to complementarity between the oligonucleotide and the viral sequence being targeted.

Other features and advantages of the invention will become more apparent from the following detailed description and claims.

DETAILED DESCRIPTION OF THE INVENTION

Definitions

As used herein, the following terms and phrases shall have the meanings set forth below:

An "oligonucleotide" or "oligo" shall mean multiple nucleotides (i.e. molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G)). The term "oligonucleotide" as used herein refers to both oligoribonucleotides (ORNs) and oligodeoxyribonucleotides (ODNs). The term. "oligonucleotide" shall also include oligonucleosides (i.e. an oligonucleotide minus the phosphate) and any other organic base containing polymer. Oligonucleotides can be obtained from existing nucleic acid sources (e.g. genomic or cDNA), but are preferably synthetic (e.g. produced by oligonucleotide synthesis).

A "stabilized oligonucledtide" shall mean an oligonucleotide that is relatively resistant to in vivo degradation (e.g. via an exo- or endo-nuclease). Preferred stabilized oligonucleotides of the instant invention have a modified phosphate backbone. Especially preferred oligonucleotides have a phosphorothioate modified phosphate backbone (i.e. at least one of the phosphate oxygens is replaced by sulfur). Other stabilized oligonucleotides include: nonionic DNA analogs, such as akyl- and aryl- phosphonates (in which the charged phosphonate oxygen is replaced by an alkyl or aryl group), phosphodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligonucleotide", "immunostimulatory CpG containing oligonucleotide", or "CpG ODN" refer to an oligonucleotide, which contains a cytosine, guanine dinucleotide sequence and stimulates (e.g. has a mitogenic effect) on vertebrate lymphocyte. Preferred immunostimulatory oligonucleotides are between 2 to 100 base pairs in size and contain a consensus mitogenic CpG motif represented by the formula:

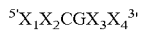

wherein C and G are unmethylated, $X_1$, $X_2$, $X_3$ and $X_4$ are nucleotides and a GCG trinucleotide sequence is not present at or near the 5' and 3' termini.

Preferably the immunostimulatory oligonucleotides range between 8 to 40 base pairs in size. In addition, the immunostimulatory oligonucleotides are preferably stabilized oligonucleotides, particularly preferred are phosphorothioate stabilized oligonucleotides. In one preferred embodiment, $X_1X_2$ is the dinucleotide GpA. In another preferred embodiment, $X_3X_4$ is preferably the dinucleotide TpC or also TpT. In a particularly preferred embodiment, the consensus motif $X_1X_2CGX_3X_4$ is preceded on the 5' end by a T. Particularly preferred consensus sequences are TGACGTT or TGACGTC.

A "neutral oligonucleotide" refers to an oligonucleotide that does not contain an unmethylated CpG or an oligonucleotide which contains a methylated CpG dinucleotide. In a preferred embodiment, a neutralizing oligonucleotide is complementary to an immunostimulatory sequence, but contains a methylated instead of an unmethylated CpG dinucleotide sequence and therefore can compete for binding with unmethylated CpG containing oligonucleotides. In a preferred embodiment, the methylation occurs at one or more of the four carbons and two nitrogens comprising the cytosine six member ring or at one or more of the five carbons and four nitrogens comprising the guanine nine member double ring. 5' methyl cytosine is a preferred methylated CpG.

An "immunoinhibitory oligonucleotide" or "immunoinhibitory CpG containing oligonucleotide" is an oligonucleotide that. Preferable immunoinhibitory oligonucleotides are between 2 to 100 base pairs in size and can be represented by the formula:

wherein X=a nucleotide and n=in the range of 0-50. In a preferred embodiment, X is a pyrimidine.

For facilitating uptake into cells, immunoinhibitory oligonucleotides are preferably in the range of 8 to 40 base pairs in size. Prolonged immunostimulation can be obtained using stabilized oligonucleotides, particularly phosphorothioate stabilized "Palindromic sequence" shall mean an inverted repeat (i.e. a sequence such as ABCDEE'D'C'B'A' in which A and A' are bases capable of forming the usual Watson-Crick base pairs. In vivo, such sequences may form double stranded structures.

An "oligonucleotide delivery complex" shall mean an oligonucleotide associated with (e.g. ionically or covalently bound to; or encapsulated within) a targeting means (e.g. a molecule that results in higher affinity binding to target cell (e.g. B-cell and natural killer (NK) cell) surfaces and/or increased cellular uptake by target cells). Examples of oligonucleotide delivery complexes include oligonucleotides associated with: a sterol (e.g. cholesterol), a lipid (e.g. a cationic lipid, virosome or liposome), or a target cell specific binding agent (e.g. a ligand recognized by target cell specific receptor). Preferred complexes must be sufficiently stable in vivo to prevent significant uncoupling prior to internalization by the target cell. However, the complex should be cleavable under appropriate conditions within the cell so that the oligonucleotide is released in a functional form.

An "immune system deficiency" shall mean a disease or disorder in which the subject's immune system is not functioning in normal capacity or in which it would be useful to boost a subject's immune response for example to eliminate a tumor or cancer (e.g. tumors of the brain, lung (e.g. small cell and non-small cell), ovary, breast prostate, colon, as well as other carcinomas and sarcomas) or a viral (e.g. HIV, herpes), fungal (e.g. *Candida* sp.), bacterial or parasitic (e.g. Leishmania, Toxoplasma) infection in a subject A "disease associated with immune system activation" shall mean a disease or condition caused or exacerbated by activation of the subject's immune system. Examples include systemic lupus erythematosus, sepsis and autoimmune diseases such as rheumatoid arthritis and multiple sclerosis.

A "subject" shall mean a human or vertebrate animal including a dog, cat, horse, cow, pig, sheep, goat, chicken, monkey, rat, mouse, etc.

Certain Unmethylated CpG Containing Oligos have B Cell Stimulatory Activity as Shown In Vitro and In Vivo In the course of investigating the lymphocyte stimulatory effects of two antisense oligonucleotides specific for endogenous retroviral sequences, using protocols described in the attached Examples 1 and 2, it was surprisingly found that two out of twenty-four "controls" (including various scrambled, sense, and mismatch controls for a panel of "antisense" ODN) also mediated B cell activation and IgM secretion, while the other "controls" had no effect Two observations suggested that the mechanism of this B cell activation by the "control" ODN may not involve antisense effects 1) comparison of vertebrate DNA sequences listed in GenBank showed no greater homology than that seen with non-stimulatory ODN and 2) the two controls showed no hybridization to Northern blots with 10 μg of spleen poly A+ RNA. Resynthesis of these ODN on a different synthesizer or extensive purification by polyacrylamide gel electrophoresis or high pressure liquid chromatography gave identical stimulation, eliminating the possibility of an impurity. Similar stimulation was seen using B cells from C3H/HeJ mice, eliminating the possibility that lipopolysaccharide (LPS) contamination could account for the results.

The fact that two "control" ODN caused B cell activation similar to that of the two "antisense" ODN raised the possibility that all four ODN were stimulating B cells through some non-antisense mechanism involving a sequence motif that was absent in all of the other nonstimulatory control ODN. In comparing these sequences, it was/discovered that all of the four stimulatory ODN contained ODN dinucleotides that were in a different sequence context from the nonstimulatory control To determine whether the CpG motif present in the stimulatory ODN was responsible for the observed stimulation, over 300 ODN ranging in length from 5 to 42 bases that contained methylated, unmethylated, or no CpG dinucleotides in various sequence contexts were synthesized. These ODNs, including the two original "controls" (ODN 1 and 2) and two originally synthesized as "antisense" (ODN 3D and 3M; Krieg; A. M. *J. Immunol.* 143:2448 (1989)), were then examined for in vitro effects on spleen cells (representative sequences are listed in Table 1). Several ODN that contained CpG dinucleotides induced B cell activation and IgM secretion; the magnitude of this stimulation typically could be increased by adding more CpG dinucleotides (Table 1; compare ODN 2 to 2a or 3D to 3Da and 3 Db). Stimulation did not appear to result from an antisense mechanism or impurity. ODN caused no detectable activation of γδ or other T cell populations.

Mitogenic ODN sequences uniformly became nonstimulatory if the CpG dinucleotide was mutated (Table 1; compare ODN 1 to 1a; 3D to. 3Dc; 3M to 3Ma; and 4 to 4a) or if the cytosine of the CpG dinucleotide was replaced by 5-methylcytosine (Table 1; ODN 1b, 2b, 2c, 3Dd, and 3 Mb). In contrast, methylation of other cytosines did not reduce ODN activity (ODN 1c, 2d, 3De and 3Mc). These data confirmed that a CpG motif is the essential element present in ODN that activate B cells.

In the course of these studies, it became clear that the bases flanking the CpG dinucleotide played an important role in determining the B cell activation induced by an ODN. The optimal stimulatory motif was determined to consist of a CpG flanked by two 5' purines (preferably a GpA dinucleotide) and two 3' pyrimidines (preferably a TpT or TpC dinucleotide). Mutations of ODN to bring the CpG motif closer to this ideal improved stimulation (e.g. compare ODN 2 to 2e; 3M to 3Md) while mutations that disturbed the motif reduced stimulation (e.g. compare ODN 3D to 3Df; 4 to 4b, 4c and 4d). On the other hand, mutations outside the CpG motif did not reduce stimulation (e.g. compare ODN 1 to 1d; 3D to 3Dg; 3M to 3Me).

Of those tested, ODNs shorter than 8 bases were nonstimulatory (e.g. ODN 4e). Among the forty-eight 8 base ODN tested, the most stimulatory sequence identified was TCAACGTT (ODN 4) which contains the self complementary "palindrome" AACGTT. In further optimizing this motif, it was found that ODN containing Gs at both ends showed increased stimulation, particularly if the the ODN were rendered nuclease resistant by phosphorothioate modification of the terminal internucleotide linkages. ODN 1585 (5' GGGGTCAACGTTCAGGGGGG 3' (SEQ ID NO:1)), in which the first two and last five internucleotide linkages are phosphorothioate modified caused an average 25.4 fold increase in mouse spleen cell proliferation compared to an average 3.2 fold increase in proliferation induced by ODN 1638, which has the same sequence as ODN 1585 except that the 10 Gs at the two ends are replaced by 10 As. The effect of the G-rich ends is cis; addition of an ODN with poly G ends but no CpG motif to cells along with 1638 gave no increased proliferation.

Other octamer ODN containing a 6 base palindrome with a TpC dinucleotide at the 5' end were also active if they were close to the optimal motif (e.g. ODN 4b,4c). Other dinucleotides at the 5' end gave reduced stimulation (eg ODN 4f; all sixteen possible dinucleotides were tested). The presence of a 3' dinucleotide was insufficient to compensate for the lack of a 5' dinucleotide (eg. ODN. 4g). Disruption of the palindrome eliminated stimulation in octamer ODN (eg., ODN 4h), but palindromes were not required in longer ODN.

TABLE 1

Oligonucleotide Stimulation of B Cells

| ODN | Sequence (5' to 3')† | Stimulation Index' | |
|---|---|---|---|
| | | ³H Uridine | IgM Production |
| 1 (SEQ ID NO: 2) | GCTAGA<u>CG</u>TTAG<u>CGT</u> | 6.1 ± 0.8 | 17.9 ± 3.6 |
| 1a (SEQ. ID NO: 3) | ......T........ | 1.2 ± 0.2 | 1.7 ± 0.5 |

TABLE 1-continued

Oligonucleotide Stimulation of B Cells

| ODN | Sequence (5' to 3')† | Stimulation Index' ³H Uridine | IgM Production |
|---|---|---|---|
| 1b (SEQ ID NO: 4) | ......Z......... | 1.2 ± 0.1 | 1.8 ± 0.0 |
| 1c (SEQ ID NO: 5) | ..........Z.. | 10.3 ± 4.4 | 9.5 ± 1.8 |
| 1d (SEQ ID NO: 6) | ..AT......GAGC. | 13.0 ± 2.3 | 18.3 ± 7.5 |
| 2 (SEQ ID NO: 7) | ATGGAAGGTCCAGCGTTCTC | 2.9 ± 0.2 | 13.6 ± 2.0 |
| 2a (SEQ ID NO: 8) | ..C..CTC..G........ | 7.7 ± 0.8 | 24.2 ± 3.2 |
| 2b (SEQ ID NO: 9) | ..Z..CTC.ZG..Z...... | 1.6 ± 0.5 | 2.8 ± 2.2 |
| 2c (SEQ ID NO: 10) | ..Z..CTC..G........ | 3.1 ± 0.6 | 7.3 ± 1.4 |
| 2d (SEQ ID NO: 11) | ..C..CTC..G.....Z.. | 7.4 ± 1.4 | 27.7 ± 5.4 |
| 2e (SEQ ID NO: 12) | ...........A...... | 5.6 ± 2.0 | ND |
| 3D (SEQ ID NO: 13) | GAGAACGCTGGACCTTCCAT | 4.9 ± 0.5 | 19.9 ± 3.6 |
| 3Da (SEQ ID NO: 14) | ........C......... | 6.6 ± 1.5 | 33.9 ± 6.8 |
| 3Db (SEQ ID NO: 15) | ........C......G.. | 10.1 ± 2.8 | 25.4 ± 0.8 |
| 3Dc (SEQ ID NO: 16) | ...C.A............ | 1.0 ± 0.1 | 1.2 ± 0.5 |
| 3Dd (SEQ ID NO: 17) | .....Z............ | 1.2 ± 0.2 | 1.0 ± 0.4 |
| 3De (SEQ ID NO: 18) | ..........Z...... | 4.4 ± 1.2 | 18.8 ± 4.4 |
| 3Df (SEQ ID NO: 19) | ......A........... | 1.6 ± 0.1 | 7.7 ± 0.4 |
| 3Dg (SEQ ID NO: 20) | ........CC.G.ACTG.. | 6.1 ± 1.5 | 18.6 ± 1.5 |
| 3M (SEQ ID NO: 21) | TCCATGTCGGTCCTGATGCT | 4.1 ± 0.2 | 23.2 ± 4.9 |
| 3Ma (SEQ ID NO: 22) | ......CT.......... | 0.9 ± 0.1 | 1.8 ± 0.5 |
| 3Mb (SEQ ID NO: 23) | .......Z.......... | 1.3 ± 0.3 | 1.5 ± 0.6 |
| 3Mc (SEQ ID NO: 24) | ..........Z........ | 5.4 ± 1.5 | 8.5 ± 2.6 |
| 3Md (SEQ ID NO: 25) | ......A..T........ | 17.2 ± 9.4 | ND |
| 3Me (SEQ ID NO: 26) | ............C..A. | 3.6 ± 0.2 | 14.2 ± 5.2 |
| 4 | TCAACGTT | 6.1 ± 1.4 | 19.2 ± 5.2 |
| 4a | ....GC.. | 1.1 ± 0.2 | 1.5 ± 1.1 |
| 4b | ...GCGC. | 4.5 ± 0.2 | 9.6 ± 3.4 |
| 4c | ...TCGA. | 2.7 ± 1.0 | ND |
| 4d | ..TT..AA | 1.3 ± 0.2 | ND |
| 4e | -....... | 1.3 ± 0.2 | 1.1 ± 0.5 |
| 4f | C....... | 3.9 ± 1.4 | ND |
| 4g | --......CT | 1.4 ± 0.3 | ND |
| 4h | ........C | 1.2 ± 0.2 | ND |
| LPS | | 7.8 ± 2.5 | 4.8 ± 1.0 |

'Stimulation indexes are the means and std. dev. derived from at least 3 separate experiments, and are compared to wells cultured with no added ODN.
ND = not done.
CpG dinucleotides are underlined.
Dots indicate identity; dashes indicate deletions.
Z indicates 5 methyl cytosine.)

The kinetics of lymphocyte activation were investigated using mouse spleen cells. When the cells were pulsed at the same time as ODN addition and harvested just four hours later, there was already a two-fold increase in $^3$H uridine incorporation. Stimulation peaked at 12-48 hours and then decreased. After 24 hours, no intact ODN were detected, perhaps accounting for the subsequent fall in stimulation when purified B cells with or without anti-IgM (at a submitogenic dose) were cultured with CpG ODN, proliferation was found to synergistically increase about 10-fold by the two mitogens in combination after 48 hours. The magnitude of stimulation was concentration dependent and consistently exceeded that of LPS under optimal conditions for both. Oligonucleotides containing a nuclease resistant phosphorothioate backbone were approximately two hundred times more potent than unmodified oligonucleotides.

Cell cycle analysis was used to determine the proportion of B cells activated by CpG-ODN. CpG-ODN induced cycling in more than 95% of B cells (Table 2). Splenic B lymphocytes sorted by flow cytometry into CD23− (marginal zone) and CD23+ (follicular) subpopulations were equally responsive to ODN-induced stimulation, as were both resting and activated populations of B cells isolated by fractionation over Percoll gradients. These studies demonstrated that CpG-ODN induce essentially all B cells to enter the cell cycle.

TABLE 2

Cell Cycle Analysis with CpG ODN

| Treatment | Percent of cells in | | |
|---|---|---|---|
| | G0 | G1 | SA + G2 + M |
| Media | 97.6 | 2.4 | 0.02 |
| ODN 1a | 95.2 | 4.8 | 0.04 |
| ODN 1d | 2.7 | 74.4 | 22.9 |
| ODN 3Db | 3.5 | 76.4 | 20.1 |
| LPS (30 μg/ml) | 17.3 | 70.5 | 12.2 |

The mitogenic effects of CpG ODN on human cells, were tested on peripheral blood mononuclear cells (PBMCs) obtained from two patients with chronic lymphocytic leukemia (CLL), as described in Example 1. Control ODN containing no CpG dinucleotide sequence showed no effect on the basal proliferation of 442 cpm and 874 cpm (proliferation measured by $^3$H thymidine incorporation) of the human cells. However, a phosphorothioate modified CpG ODN 3Md (SEQ ID NO: 25) induced increased proliferation of 7210 and 86795 cpm respectively in the two patients at a concentration of just 1 μM. Since these cells had been frozen, they may have been less responsive to the oligos than fresh cells in vivo. In addition, cells from CLL patients typically are non-proliferating, which is why traditional chemotherapy is not effective.

Certain B cell lines such as WEHI-231 are induced to undergo growth arrest and/or apoptosis in response to crosslinking of their antigen receptor by anti-IgM (Jakway, J. P. et al., "Growth regulation of the B lymphoma cell line WEHI-231 by anti-immunoglobulin, lipopolysaccharide and other bacterial products" *J. Immunol.* 137: 2225 (1986); Tsubata, T., J. Wu and T. Honjo: B-cell apoptosis induced by antigen receptor crosslinking is blocked by a T-cell signal through CD40." *Nature* 364: 645 (1993)). WEHI-231 cells are rescued from this growth arrest by certain stimuli such as LPS and by the CD40 ligand. ODN containing the CpG motif were also found to protect WEHI-231 from anti-IgM induced growth arrest, indicating that accessory cell populations are not required for the effect.

To better understand the immune effects of unmethylated CpG ODN, the levels of cytokines and prostaglandins in vitro and in vivo were measured. Unlike LPS, CpG ODN were not found to induce purified macrophages to produce prostaglandin PGE2. In fact, no apparent direct effect of CpG ODN was detected on either macrophages or T cells. In vivo or in whole spleen cells, no significant increase in the following interleukins: IL-2, IL-3, IL4, or IL-10 was detected within the first six hours. However, the level of IL-6 increased strikingly within 2 hours in the serum of mice injected with CpG ODN. Increased expression of IL-12 and interferon gamma (IFN-γ) by spleen cells was also detected within the first two hours.

To determine whether CpG ODN can cause in vivo immune stimulation, DBA/2 mice were injected once intraperitoneally with PBS or phosphorothioate CpG or non-CpG ODN at a dose of 33 mg/kg (approximately 500 μg/mouse). Pharmacokinetic studies in mice indicate that this dose of phosphorothioate gives levels of approximately 10 μg/g in spleen tissue (within the effective concentration range determined from the in vitro studies described herein) for longer than twenty-four-hours (Agrawal, S. et al. (1991) *Proc. Natl. Acad. Sci. USA* 91:7595). Spleen cells from mice were examined twenty-four hours after ODN injection for expression of B cells surface activation markers Ly-6A/E, Bla-1, and class II MHC using three color flow cytometry and for their spontaneous proliferation using $^3$H thymidine: Expression of all three activation markers was significantly increased in B cells from mice injected with CpG ODN, but not from mice injected with PBS or non-CpG ODN. Spontaneous $^3$H thymidine incorporation was increased by 2-6 fold in spleen cells from mice injected with the stimulatory ODN compared to PBS or non-CpG ODN-injected mice. After 4 days, serum IgM levels in mice injected with CpG ODN in vivo were increased by approximately 3-fold compared to controls. Consistent with the inability of these agents to activate T cells, there was minimal change in T cell expression of the IL-2R or CD44.

Degradation of phophodiester ODN in serum is predominantly mediated by 3' exonucleases, while intracellular ODN degradation is more complex, involving 5' and 3' exonucleases and endonucleases. Using a panel of ODN bearing the 3D sequence with varying numbers of phosphorothioate modified linkages at the 5' and 3' ends, it was empirically determined that two 5' and five 3' modified linkages are required to provide optimal stimulation with this CpG ODN.

Unmethylated CpG Containing Oligos have NK Cell Stimulatory Activity

As described in further detail in Example 4, experiments were conducted to determine whether CpG containing oligo-nucleotides stimulated the activity of natural killer (NK) cells in addition to B cells. As shown in Table 3, a marked induction of NK activity among spleen cells cultured with CpG ODN 1 and 3Dd was observed. In contrast, there was relatively no induction in effectors that had been treated with non-CpG control ODN.

TABLE 3

Induction Of NK Activity By CpG Oligodeoxynucleotides (ODN)

| ODN | % YAC-1 Specific Lysis* Effector:Target | | % 2C11 Specific Lysis Effector:Target | |
|---|---|---|---|---|
| | 50:1 | 100:1 | 50:1 | 100:1 |
| None | −1.1 | −1.4 | 15.3 | 16.6 |
| 1 | 16.1 | 24.5 | 38.7 | 47.2 |

TABLE 3-continued

Induction Of NK Activity By CpG Oligodeoxynucleotides (ODN)

| ODN | % YAC-1 Specific Lysis* Effector:Target | | % 2C11 Specific Lysis Effector:Target | |
|---|---|---|---|---|
| | 50:1 | 100:1 | 50:1 | 100:1 |
| 3Dd | 17.1 | 27.0 | 37.0 | 40.0 |
| non-CpG ODN | −1.6 | −1.7 | 14.8 | 15.4 |

Neutralizing Activity of Methylated CpG Containing Oligos

B cell mitogenicity of ODN in which cytosines in CpG motifs or elsewhere were replaced by 5-methylcytosine were tested as described in Example 1. As shown in Table 1 above, ODN containing methylated CpG motifs were non-mitogenic (Table 1; ODN 1c, 2f, 3De, and 3Mc). However, methylation of cytosines other than in a CpG dinucleotide retained their stimulatory properties (Table 1, ODN 1d, 2d, 3Df, and 3Md).

Immunoinhibitory Activity of Oligos Containing a GCG Trinucleotide Sequence at or Near Both Termini In some cases, ODN containing CpG dinucleotides that are not in the stimulatory motif described above were found to block the stimulatory effect of other mitogenic CpG ODN. Specifically the addition of an atypical CpG motif consisting of a GCG near or at the 5' and/or 3' end of CpG ODN actually inhibited stimulation of proliferation by other CpG motifs. Methylation or substitution of the cytosine in a GCG motif reverses this effect. By itself, a GCG motif in an ODN has a modest mitogenic effect, though far lower than that seen with the preferred CpG motif.

Proposed Mechanisms of Action of Immunostimulatory, Neutralizing and Immunoinhibitory Oligonucleotides Unlike antigens that trigger B cells through their surface Ig receptor, CpG-ODN did not induce any detectable $Ca^{2+}$ flux, changes in protein tyrosine phosphorylation, or IP 3 generation. Flow cytometry with FITC-conjugated ODN with or without a CpG motif was performed as described in Zhao, Q et al., (*Antisense Research and Development* 3:53-66 (1993)), and showed equivalent membrane binding, cellular uptake, efflux, and intracellular localization. This suggests that there may not be cell membrane proteins specific for CpG ODN. Rather than acting through the cell membrane, that data suggests that unmethylated CpG containing oligonucleotides require cell uptake for activity: ODN covalently linked to a solid Teflon support were nonstimulatory, as were biotinylated ODN immobilized on either avidin beads or avidin coated petri dishes. CpG ODN conjugated to either FITC or biotin retained full mitogenic properties, indicating no steric hindrance.

The optimal CpG motif (TGACGTT/C is identical to the CRE (cyclic AMP response element). Like the mitogenic effects of CpG ODN, binding of CREB to the CRE is abolished if the central CpG is methylated. Electrophoretic mobility shift assays were used to determine whether CpG ODN, which are single stranded, could compete with the binding of B cell CREB/ATF proteins to their normal binding site, the doublestranded CRE. Competition assays demonstrated that single stranded ODN containing CpG motifs could completely compete the binding of CREB to its binding site, while ODN without CpG motifs could not. These data support the conclusion that CpG ODN exert their mitogenic effects through interacting with one or more-B cell CREB/ATF proteins in some way. Conversely, the presence of GCG sequences or other atypical CPG motifs near the 5' and/or 3' ends of ODN likely interact with CREB/ATF proteins in away that does not cause activation, and may even prevent it.

The stimulatory CpG motif is common in microbial genomic DNA, but quite rare in vertebrate DNA. In addition, bacterial DNA has been reported to induce B cell proliferation and immunoglobulin (Ig) production, while mammalian DNA does not (Messina, J. P. et al., *J. Immunol.* 147:1759 (1991)). Experiments further described in Example 3, in which methylation of bacterial DNA with CpG methylase was found to abolish mitogenicity, demonstrates that the difference in CpG status is the cause of B cell stimulation by bacterial DNA. This data supports the following conclusion: that unmethylated CpG dinucleotides present within bacterial DNA are responsible for the stimulatory effects of bacterial DNA.

Teleologically, it appears likely that lymphocyte activation by the CpG motif represents an immune defense mechanism that can thereby distinguish bacterial from host DNA. Host DNA would induce little or no lymphocyte activation due to it CpG suppression and methylation. Bacterial DNA would cause selective lymphocyte activation in infected tissues. Since the CpG pathway synergizes with B cell activation through the antigen receptor, B cells bearing antigen receptor specific for bacterial antigens would receive one activation signal through cell membrane Ig and a second signal from bacterial DNA, and would therefore tend to be preferentially activated. The interrelationship of this pathway with other pathways of B cell activation provide a physiologic mechanism employing a polyclonal antigen to induce antigen-specific responses.

Method for Making Immunostimulatory Oligos

For use in the instant invention, oligonucleotides can be synthesized de novo using any of a number of procedures well known in the art. For example, the β-cyanoethyl phosphoramidite method (S. L. Beaucage and M. H. Caruthers, (1981) *Tet. Let.* 22:1859); nucleoside H-phosphonate method (Garegg-et al., (1986) *Tet. Let.* 27: 4051-4054; Froehler et al., (1986) *Nucl. Acid Res.* 14: 5399-5407; Garegg et al., (1986) *Tet. Let.* 27: 4055-4058, Gaffney et al., (1988) *Tet. Let.* 29:2619-2622). These chemistries can be performed by a variety of automated oligonucleotide synthesizers available in the market. Alternatively, oligonucleotides can be prepared from existing nucleic acid sequences (e.g. genomic or cDNA) using known techniques, such as those employing restriction enzymes, exonucleases or endonucleases.

For use in vivo, oligonucleotides are preferably relatively resistant to degradation (e.g. via endo- and exo- nucleases). Oligonucleotide stabilization can be accomplished via phosphate backbone modifications. A preferred stabilized oligonucleotide has a phosphorothioate modified backbone. The pharmacokinetics of phosphorothioate ODN show that they have a systemic half-life of forty-eight hours in rodents and suggest that they may be useful for in vivo applications (Agrawal, S. et al. (1991) *Proc. Natl. Acad. Sci. USA* 88:7595). Phosphorothioates may be synthesized using automated techniques employing either phosphoramidate or H phosphonate chemistries. Aryl- and alkyl- phosphonates can be made e.g. (as described in U.S. Pat. No. 4,469,863); and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described Uhlmann, E. and Peyman, A (1990) *Chem. Rev.* 90:544; Goodchild, J. (1990) *Bioconjugate Chem.* 1:165).

For administration in vivo, oligonucleotides may be associated with a molecule that results in higher affinity binding to target cell (e.g. B-cell and natural killer (NK) cell) surfaces and/or increased cellular uptake by target cells to form an "oligonucleotide delivery complex". Oligonucleotides can be ionically, or covalently associated with appropriate molecules using techniques which are well known in the art. A variety of coupling or crosslinking agents can be used e.g. protein A, carbodiimide, and N-succinimidyl-3-(2-pyridyldithio) propionate (SPDP). Oligonucleotides can alternatively be encapsulated in liposomes or virosomes using well-known techniques.

The present invention is further illustrated by the following Examples which in no way should be construed as further limiting. The entire contents of all of the references (including literature references, issued patents, published patent applications, and co-pending patent applications) cited throughout this application are hereby expressly incorporated by reference.

Therapeutic Uses of Immunostimulatory Oligos

Based on their immunostimulatory properties, oligonucleotides containing at least one unmethylated CpG dinucleotide can be administered to a subject in vivo to treat an "immune system deficiency". Alternatively, oligonucleotides containing at least one unmethylated CpG dinucleotide can be contacted with lymphocytes (e.g. B cells or NK cells) obtained from a subject having an immune system deficiency ex vivo and activated lymphocytes can then be reimplanted in the subject Immunostimulatory oligonucleotides can also be administered to a subject in conjunction with a vaccine, as an adjuvant, to boost a subject's immune system to effect better response from the vaccine. Preferably the unmethylated CpG dinucleotide is administered slightly before or at the same time as the vaccine.

Preceding chemotherapy with an immunostimulatory oligonucleotide should prove useful for increasing the responsiveness of the malignant cells to subsequent chemotherapy. CpG ODN also increased natural killer cell activity in both human and murine cells. Induction of NK activity may likewise be beneficial in cancer immunotherapy.

Therapeutic Uses for Neutral Oligonucleotides

Oligonucleotides that are complementary to certain target sequences can be synthesized and administered to a subject in vivo. For example, antisense oligonucleotides hybridize to complementary mRNA, thereby preventing expression of a specific target gene. The sequence-specific effects of antisense oligonucleotides have made them useful research tools for the investigation of protein function. Phase I/II human trials of systemic antisense therapy are now underway for acute myelogenous leukemia and HIV.

In addition, oligonucleotide probes (i.e. oligonucleotides with a detectable label) can be administered to a subject to detect the presence of a complementary sequence based on detection of bound label. In vivo administration and detection of oligonucleotide probes may be useful for diagnosing certain diseases that are caused or exacerbated by certain DNA sequences (e.g. systemic lupus erythematosus, sepsis and autoimmune diseases).

Antisense oligonucleotides or oligonucleotide probes in which any or all CpG dinucleotide is methylated, would not produce an immune reaction when administered to a subject in vivo and therefore would be safer than the corresponding non-methylated CpG containing oligonucleotide.

For use in therapy, an effective amount of an appropriate oligonucleotide alone or formulated as an oligonucleotide delivery complex can be administered to a subject by any mode allowing the oligonucleotide to be taken up by the appropriate target cells (e.g. B-cells and NK cells). Preferred routes of administration include oral and transdermal (e.g. via a patch). Examples of other routes of administration include injection (subcutaneous, intravenous, parenteral, intraperitoneal, intrathecal, etc.). The injection can be in a bolus or a continuous infusion.

An oligonucleotide alone or as an oligonucleotide delivery complex can be administered in conjunction with a pharmaceutically acceptable carrier. As used herein, the phrase "pharmaceutically acceptable carrier" is intended to include substances that can be coadministered with an oligonucleotide or an oligonucleotide delivery complex and allows the oligonucleotide to perform its intended function. Examples of such carriers include solutions, solvents, dispersion media, delay agents, emulsions and the like. The use of such media for pharmaceutically active substances are well known in the art. Any other conventional carrier suitable for use with the oligonucleotides falls within the scope of the instant invention.

The language "effective amount" of an oligonucleotide refers to that amount necessary or sufficient to realize a desired biologic effect. For example, an effective amount of an oligonucleotide containing at least one methylated CpG for treating an immune system deficiency could be that amount necessary to eliminate a tumor, cancer, or bacterial, viral or fungal infection. An effective amount for use as a vaccine adjuvant could be that amount useful for boosting a subject's immune response to a vaccine. An "effective amount" of an oligonucleotide lacking a non-methylated CpG for use in treating a disease associated with immune system activation, could be that amount necessary to outcompete non-methylated CpG containing nucleotide sequences. The effective amount for any particular application can vary depending on such factors as the disease or condition being treated, the particular oligonucleotide being administered, the size of the subject, or the severity of the disease or condition. One of ordinary skill in the art can empirically determine the effective amount of a particular oligonucleotide without necessitating undue experimentation.

The studies reported above indicate that unmethylated CpG containing oligonucleotides are directly mitogenic for lymphocytes (e.g. B cells and NK cells). Together with the presence of these sequences in bacterial DNA, these results suggest that the underrepresentation of CpG dinucleotides in animal genomes, and the extensive methylation of cytosines present in such dinucleotides, may be explained by the existence of an immune defense mechanism that can distinguish bacterial from host DNA. Host DNA would commonly be present in many anatomic regions and areas of inflammation due to apoptosis (cell death), but generally induces little or no lymphocyte activation. However, the presence of bacterial DNA containing unmethylated CpG motifs can cause lymphocyte activation precisely in infected anatomic regions, where it is beneficial. This novel activation pathway provides a rapid alternative to T cell dependent antigen specific B cell activation. However, it is likely that B cell activation would not be totally nonspecific. B cells bearing antigen receptors specific for bacterial products could receive one activation signal through cell membrane Ig, and a second from bacterial DNA, thereby more vigorously triggering antigen specific immune responses.

As with other immune defense mechanisms, the response to bacterial DNA could have undesirable consequences in some settings. For example, autoimmune responses to self antigens would also tend to be preferentially triggered by bacterial infections, since autoantigens could also provide a second activation signal to autoreactive B cells triggered by bacterial DNA. Indeed the induction of autoimmunity by bacterial infections is a common clinical observance. For example, the autoimmune disease systemic lupus erythematosus, which is: i) characterized by the production of anti-DNA antibodies; ii) induced by drugs which inhibit DNA methyltransferase (Cornacchia, E. J. et al., *J. Clin Invest.* 92:38 (1993)); and iii) associated with reduced DNA methylation (Richardson, B., L. et al., *Arth. Rheum* 35:647 (1992)), is likely triggered at least in part by activation of DNA-specific B cells through stimulatory signals provided by CpG motifs, as well as by binding of bacterial DNA to antigen receptors.

Further, sepsis, which is characterized by high morbidity and mortality due to massive and nonspecific activation of the immune system may be initiated by bacterial DNA and other products released from dying bacteria that reach concentrations sufficient to directly activate many lymphocytes.

Lupus, sepsis and other "diseases associated with immune system activation" may be treated, prevented or ameliorated by administering to a subject oligonucleotides lacking an unmethylated CpG dinucleotide (e.g. oligonucleotides that do not include a CpG motif or oligonucleotides in which the CpG motif is methylated) to block the binding of unmethylated CpG containing nucleic acid sequences. Oligonucleotides lacking an unmethylated CpG motif can be administered alone or in conjunction with compositions that block an immune cell's reponse to other mitogenic bacterial products (e.g. LPS).

The following serves to illustrate mechanistically how oligonucleotides containing an unmethylated CpG dinucleotide can treat, prevent or ameliorate the disease lupus. Lupus is commonly thought to be triggered by bacterial or viral infections. Such infections have been reported to stimulate the production of nonpathogenic antibodies to single stranded DNA. These antibodies likely recognize primarily bacterial sequences including unmethylated CpGs. As disease develops in lupus, the anti-DNA antibodies shift to pathogenic antibodies that are specific for double-stranded DNA. These antibodies would have increased binding for methylated CpG sequences and their production would result from a breakdown of tolerance in lupus. Alternatively, lupus may result when a patient's DNA becomes hypomethylated, thus allowing anti-DNA antibodies specific for unmethylated CpGs to bind to self DNA and trigger more widespread autoimmunity through the process referred to as "epitope spreading".

In either case, it may be possible to restore tolerance in lupus patients by coupling antigenic oligonucleotides to a protein carrier such as gamma globulin (IgG). Calf-thymus DNA complexed to gamma globulin has been reported to reduce anti-DNA antibody formation.

Therapeutic Uses of Oligos Containing GCG Trinucleotide Sequences at or Near Both Termini Based on their interaction with CREB/ATF, oligonucleotides containing GCG trinucleotide sequences at or near both termini have antiviral activity, independent of any antisense effect due to complementarity between the oligonucleotide and the viral sequence being targeted. Based on this activity, an effective amount of inhibitory oligonucleotides can be administered to a subject to treat or prevent a viral infection.

EXAMPLES

Example 1

Effects of ODNs on B Cell Total RNA Synthesis and Cell Cycle

B cells were purified from spleens obtained from 6-12 wk old specific pathogen free DBA/2 or BXSB mice (bred in the University of Iowa animal care facility; no substantial strain differences were noted) that were depleted of T cells with anti-Thy-1.2 and complement and centrifugation over lympholyte M (Cedarlane Laboratories, Hornby, Ontario, Canada) ("B cells"). B cells contained fewer than 1% CD4$^+$ or CD8$^+$ cells. 8×10$^4$ B cells were dispensed in triplicate into 96 well microtiter plates in 100 µl RPMI containing 10% FBS (heat inactivated to 65° C. for 30 min.), 50 µM 2-mercaptoethanol, 100 U/ml penicillin, 100 ug/ml streptomycin, and 2 mM L-glutamate. 20 µM ODN were added at the start of culture for 20 h at 37° C., cells pulsed with 1 µCi of $^3$H uridine, and harvested and counted 4 hr later. Ig secreting B cells were enumerated using the ELISA spot assay after culture of whole spleen cells with ODN at 20 µM for 48 hr. Data, reported in Table 1, represent the stimulation index compared to cells cultured without ODN. Cells cultured without ODN gave 687 cpm, while cells cultured with 20 µg/ml LPS (determined by titration to be the optimal concentration) gave 99,699 cpm in this experiment. $^3$H thymidine incorporation assays showed similar results, but with some nonspecific inhibition by thymidine released from degraded ODN (Matson. S and A. M. Krieg (1992) Nonspecific suppression of $^3$H-thymidine incorporation by control oligonucleotides. *Antisense Research and Development* 2:325).

For cell cycle analysis, 2×10$^6$ B cells were cultured for 48 hr. in 2 ml tissue culture medium alone, or with 30 µg/ml LPS or with the indicated phosphorothioate modified ODN at 1 µM. Cell cycle analysis was performed as described in (Darzynkiewicz, Z. et al., *Proc. Natl. Acad. Sci. USA* 78:2881 (1981)).

To test the mitogenic effects of CpG ODN on human cells, perpheral blood monocyte cells (PBMCs) were obtained from two patients with chronic lymphocytic leukemia (CLL), a disease in which the circulating cells are malignant B cells. Cells were cultured for 48 hrs and pulsed for 4 hours with tritiated thymidine as described above.

Example 2

Effects of ODN on Production of IgM from B cells

Single cell suspensions from the spleens of freshly killed mice were treated with anti-Thyl, anti-CD4, and anti-CD8 and complement by the method of Leibson et al., *J. Exp. Med.* 154:1681 (1981)). Resting B cells (<02% T cell contamination) were isolated from the 63-70% band of a discontinuous Percoll gradient by the procedure of DeFranco et al, *J. Exp. Med.* 155:1523 (1982). These were cultured as described above in 30 µM ODN or 20 µg/ml LPS for 48 hr. The number of B cells actively secreting IgM was maximal at this time point, as determined by ELIspot assay (Klinman D. M. et al. *J. Immunol.* 144:506 (1990)). In that assay, B cells were incubated for 6 hrs on anti-Ig coated microtiter plates. The Ig they produced (>99% IgM) was detected using phosphatase-labelled anti-Ig (Southern Biotechnology Associated, Birmingham, Ala.). The antibodies produced by individual B cells were visualized by addition of BCIP (Sigma Chemical Co., St. Louis Mo.) which forms an insoluble blue precipitate in the presence of phosphatase. The dilution of cells producing 20-40 spots/well was used to determine the total number of antibody-secreting B cells/sample. All assays were performed in triplicate. In some experiments, culture supernatants were assayed for IgM by ELISA, and showed similar increases in response to CpG-ODN.

table 1

Example 3

B Cell Stimulation by Bacterial DNA

DBA/2 B cells were cultured with no DNA or 50 µg/ml of a) *Micrococcus lysodeikticus*; b) NZB/N mouse spleen; and c) NFS/N mouse spleen genomic DNAs for 48 hours, then pulsed with $^3$H thymidine for 4 hours prior to cell harvest. Duplicate DNA samples were digested with DNAse I for 30 minutes at 37 C prior to addition to cell cultures. *E coli* DNA also induced an 8.8 fold increase in the number of IgM secreting B cells by 48 hours using the ELISA-spot assay.

DBA/2 B cells were cultured with either no additive, 50 µg/ml LPS or the ODN 1; 1a; 4; or 4a at 20 µM. Cells were cultured and harvested at 4, 8, 24 and 48 hours. BXSB cells were cultured as in Example 1 with 5, 10, 20, 40 or 80 µM of ODN 1; 1a; 4; or 4a or LPS. In this experiment, wells with no ODN had 3833 cpm. Each experiment was performed at least three times with similar results. Standard deviations of the triplicate wells were <5%.

Example 4

Effects of ODN on Natural Killer (NK) Activity $10\times10^6$ C57BL/6 spleen cells were cultured in two ml RPMI (supplemented as described for Example 1) with or without 40 µM CpG or non-CpG ODN for forty-eight hours. Cells were washed, and then used as effector cells in a short term $^{51}$Cr release assay with YAC-1 and 2C11, two NK sensitive target cell lines (Ballas, Z. K. et al. (1993) *J. Immunol.* 150:17). Effector cells were added at various concentrations to $10^4$ $^{51}$Cr-labeled target cells in V-bottom microtiter plates in 0.2 ml, and incubated in 5% CO$_2$ for 4 hr. at 37° C. Plates were then centrifuged, and an aliquot of the supernatant counted for radioactivity. Percent specific lysis was determined by calculating the ratio of the $^{51}$Cr released in the presence of effector cells minus the $^{51}$Cr released when the target cells are cultured alone, over the total counts released after cell lysis in 2% acetic acid minus the $^{51}$Cr cpm released when the cells are cultured alone.

Example 5

In Vivo Studies with CpG Phosphorothioate ODN

Mice were weighed and injected IP with 0.25 ml of sterile PBS or the indicated phophorothioate ODN dissolved in PBS. Twenty four hours later, spleen cells were harvested, washed, and stained for flow cytometry using phycoerythrin conjugated 6B2 to gate on B cells in conjunction with biotin conjugated anti Ly-6A/E or anti-Ia$^d$ (Pharmingen, San Diego, Calif.) or anti-Bla-1 (Hardy, R. R et al., *J. Exp. Med.* 159:1169 (1984). Two mice were studied for each condition and analyzed individually.

Example 6

Titration of Phosphorothioate ODN for B Cell Stimulation

B cells were cultured with phosphorothioate ODN with the sequence of control ODN 1a or the CpG ODN 1d and 3 Db and then either pulsed after 20 hr with $^3$H uridine or after 44 hr with $^3$H thymidine before harvesting and determining cpm.

Example 7

Rescue of B Cells From Apoptosis

WEHI-231 cells ($5\times10^4$/well) were cultured for 1 hr. at 37 C in the presence or absence of LPS or the control ODN 1a or the CpG ODN. 1d and 3 Db before addition of anti-IgM (1 µ/ml). Cells were cultured for a further 20 hr. before a 4 hr. pulse with 2 µCi/well $^3$H thymidine. In this experiment, cells with no ODN or anti-IgM gave $90.4\times10^3$ by addition of anti-IgM. The phosphodiester ODN shown in Table 1 gave similar protection, though with some nonspecific suppression due to ODN degradation. Each experiment was repeated at least 3 times with similar results.

Example 8

In Vivo Induction of IL-6

DBA/2 female mice (2 mos. old) were injected 1P with 500 µg CpG or control phosphorothioate ODN. At various time points after injection, the mice were bled. Two mice were studied for each time point. IL-6 was measured by Elisa, and IL-6 concentration was calculated by comparison to a standard curve generated using recombinant IL-6. The sensitivity of the assay was 10 pg/ml. Levels were undetectable after 8 hr.

Example 9

Binding of B cell CREB/ATF to a Radiolabelled Doublestranded CRE Probe (CREB).

Whole cell extracts from CH12.LX B cells showed 2 retarded bands when analyzed by EMSA with the CRE probe (free probe is off the bottom of the figure). The CREB/ATF protein(s) binding to the CRE were competed by the indicated amount of cold CRE, and by single-stranded CpG ODN, but not by non-CpG ODN.

Equivalents

Those skilled in the art will recognize, or be able to ascertain using no more than routine experimentation, many equivalents of the specific embodiments of the invention described herein. Such equivalents are intended to be encompassed by the following claims.

The invention claimed is:

1. A method of increasing interferon-gamma in a subject comprising administering to a subject an immunostimulatory oligonucleotide/ delivery complex, said complex comprising an immunostimulatory oligonucleotide linked to a biodegradable delivery complex, wherein the immunostimulatory oligonucleotide is 8 to 40 nucleotides in length, has greater than two unmethylated cytosine-guanine dinucleotides and comprises 5' $X_1X_2CGX_3X_4$ 3', wherein C and G are unmethylated and $X_1$, $X_2$ are nucleotides, and $X_3$ and $X_4$ are pyrimidines, in an amount sufficient to increase interferon-gamma in said subject.

2. The method of claim 1, wherein said delivery complex is a liquid phase microcarrier.

3. The method of claim 1, wherein said immunostimulatory oligonucleotide is covalently linked to said delivery complex.

4. The method of claim 1, wherein said immunostimulatory oligonucleotide is non-covalently linked to said delivery complex.

5. The method of claim 1, wherein said immunostimulatory oligonucleotide comprises a phosphate backbone modification.

6. The method of claim 5, wherein said phosphate backbone modification is a phosphorothioate.

7. The method of claim 1, wherein the immunostimulatory oligonucleotide does not include a GCG trinucleotide at a 5' and/or 3' terminal.

* * * * *

SEQUENCE LISTING

<160> NUMBER OF SEQ ID NOS: 27

<210> SEQ ID NO 1
<211> LENGTH: 20
<212> TYPE: DNA

<213> ORGANISM: Artificial Sequence
<220> FEATURE:
<223> OTHER INFORMATION: Synthetic oligonucleotide

<400> SEQUENCE: 1
ggggtcaacg ttcagggggg                                          20

<210> SEQ ID NO 2
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 2
gctagacgtt agcgt                                               15

<210> SEQ ID NO 3
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 3
gctagatgtt agcgt                                               15

<210> SEQ ID NO 4
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)...(7)
<223> OTHER INFORMATION: m5c

<400> SEQUENCE: 4
gctagangtt agcgt                                               15

<210> SEQ ID NO 5
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (13)...(13)
<223> OTHER INFORMATION: m5c

<400> SEQUENCE: 5
gctagacgtt agngt                                               15

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 6
gcatgacgtt gagct                                               15

<210> SEQ ID NO 7
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 7
atggaaggtc cagcgttctc                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
atcgactctc gagcgttctc                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)...(3)
<223> OTHER INFORMATION: m5c
<220> FEATURE:
<221> NAME/KEY: modified_base
<222> LOCATION: (10)...(10)
<223> OTHER INFORMATION: m5c
<220> FEATURE:
<221> NAME/KEY: modified_base
<222> LOCATION: (14)...(14)
<223> OTHER INFORMATION: m5c

<400> SEQUENCE: 9
atngactctn gagngttctc                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)...(3)
<223> OTHER INFORMATION: m5c

<400> SEQUENCE: 10
atngactctc gagcgttctc                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (18)...(18)
<223> OTHER INFORMATION: m5c

<400> SEQUENCE: 11
atcgactctc gagcgttntc                                               20

<210> SEQ ID NO 12
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 12
atggaaggtc caacgttctc                                          20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
gagaacgctg gaccttccat                                          20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
gagaacgctc gaccttccat                                          20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
gagaacgctc gaccttcgat                                          20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
gagcaagctg gaccttccat                                          20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (6)...(6)
<223> OTHER INFORMATION: m5c

<400> SEQUENCE: 17
gagaangctg gaccttccat                                          20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: modified_base
<222> LOCATION: (14)...(14)
<223> OTHER INFORMATION: m5c

<400> SEQUENCE: 18
gagaacgctg gacnttccat                                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
gagaacgatg gaccttccat                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gagaacgctc cagcactgat                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
tccatgtcgg tcctgatgct                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
tccatgctgg tcctgatgct                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)...(8)
<223> OTHER INFORMATION: m5c

<400> SEQUENCE: 23
tccatgtngg tcctgatgct                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: modified_base
<222> LOCATION: (12)...(12)
<223> OTHER INFORMATION: m5c

<400> SEQUENCE: 24
tccatgtcgg tnctgatgct                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
tccatgacgt tcctgatgct                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
tccatgtcgg tcctgctgat                                               20

<210> SEQ ID NO 27
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 27
gggtcaagtc tgagggggg                                                19
```